United States Patent
Gell et al.

(10) Patent No.: US 6,997,915 B2
(45) Date of Patent: Feb. 14, 2006

(54) SANITARY NAPKIN WITH ADJUSTABLE LENGTH INTERGLUTEAL STRIP

(75) Inventors: Carol B. Gell, Belle Mead, NJ (US); Safiyya Shabazz-Houston, Philadelphia, PA (US); James P. Barr, East Amwell, NJ (US); Tara Glasgow, New Hope, PA (US); Raymond J. Hull, Jr., Hampton, NJ (US); Marina Nikitina, New Britain, PA (US); Pramod S. Mavinkurve, Princeton, NJ (US); Kenneth Anthony Pelley, Hopewell, NJ (US); Kendra S. Rose, Philadelphia, PA (US); Martha Taylor, Mercerville, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 462 days.

(21) Appl. No.: 09/879,494

(22) Filed: Jun. 12, 2001

(65) Prior Publication Data

US 2002/0193766 A1 Dec. 19, 2002

(51) Int. Cl.
*A61F 13/15* (2006.01)

(52) U.S. Cl. .............................. 604/385.16; 604/385.17; 604/385.01

(58) Field of Classification Search ............ 604/385.01, 604/385.14, 385.16, 385.17
See application file for complete search history.

(56) References Cited

U.S. PATENT DOCUMENTS

| 2,295,016 A | 9/1942 | Scribner |
| 2,742,903 A | 4/1956 | Lightner |
| RE24,385 E | 10/1957 | Flanders |
| D191,649 S | 10/1961 | Dudley |

(Continued)

FOREIGN PATENT DOCUMENTS

| CH | 643730 A | 6/1984 |
| DE | 298 08 968 A | 9/1998 |
| GB | 0 860 148 A | 2/1961 |
| WO | WO 90/04956 A1 | 5/1990 |
| WO | WO 97/01997 A1 | 1/1997 |
| WO | WO 97/03623 A2 | 2/1997 |
| WO | WO 98/51249 A1 | 11/1998 |

OTHER PUBLICATIONS

European Search Report dated Feb. 13, 2004, for corresponding Appln. No. EP 02254039.7.

*Primary Examiner*—Larry I. Schwartz
*Assistant Examiner*—C. Lynne Anderson

(57) ABSTRACT

A sanitary napkin has a strip that extends rearwardly to reside in the intergluteal crevice. The pad is sized and configured to fit snugly against the wearer's body without penetrating the vaginal orifice. The strip provides improved body contact thus providing similar protection with a smaller pad and a discretion benefit to the user. The invention provides various alternative mechanisms for varying the length of the strip by the user.

28 Claims, 28 Drawing Sheets

U.S. PATENT DOCUMENTS

| | | | |
|---|---|---|---|
| 3,375,826 A | 4/1968 | Field | |
| D215,386 S | 9/1969 | Glassman | |
| D234,162 S | 1/1975 | Andersen | |
| D236,385 S | 8/1975 | Celander et al. | |
| 3,906,952 A | 9/1975 | Zamist | |
| D240,562 S | 7/1976 | Whitehead et al. | |
| D240,563 S | 7/1976 | Whitehead et al. | |
| D240,564 S | 7/1976 | Whitehead et al. | |
| D247,368 S | 2/1978 | Whitehead | |
| 4,072,151 A | 2/1978 | Levine | |
| 4,184,498 A | 1/1980 | Franco | |
| 4,484,919 A | 11/1984 | Sohn et al. | |
| 4,533,357 A | 8/1985 | Hall | |
| 4,556,146 A | 12/1985 | Swanson et al. | |
| 4,596,570 A * | 6/1986 | Jackson et al. | 604/387 |
| 4,597,759 A * | 7/1986 | Johnson | 604/385.16 |
| 4,687,478 A | 8/1987 | Van Tilburg | |
| 4,753,648 A * | 6/1988 | Jackson | 604/389 |
| 4,900,319 A | 2/1990 | Richwine | |
| 4,950,264 A | 8/1990 | Osborn, III | |
| 4,964,860 A | 10/1990 | Gipson et al. | |
| 5,009,653 A | 4/1991 | Osborn, III | |
| 5,100,399 A | 3/1992 | Janson et al. | |
| 5,106,385 A | 4/1992 | Allen et al. | |
| 5,261,901 A | 11/1993 | Guay | |
| 5,267,992 A | 12/1993 | Van Tilburg | |
| 5,295,986 A | 3/1994 | Zehner et al. | |
| 5,305,162 A | 4/1994 | Kushiro et al. | |
| 5,374,262 A | 12/1994 | Keuhn, Jr. et al. | |
| 5,383,868 A | 1/1995 | Hyun | |
| 5,445,628 A | 8/1995 | Gipson et al. | |
| D366,524 S | 1/1996 | Chung | |
| 5,489,282 A | 2/1996 | Zehner et al. | |
| 5,520,675 A | 5/1996 | Knox-Sigh | |
| 5,683,373 A | 11/1997 | Darby | |
| 5,713,886 A | 2/1998 | Sturino | |
| D392,736 S | 3/1998 | Erickson | |
| 5,729,835 A | 3/1998 | Williams | |
| D394,503 S | 5/1998 | Perrini | |
| D395,504 S | 6/1998 | Darby | |
| D395,508 S | 6/1998 | Darby | |
| 5,772,649 A | 6/1998 | Siudzinski | |
| 5,827,261 A | 10/1998 | Osborn, III et al. | |
| 5,843,267 A | 12/1998 | Cashaw et al. | |
| 5,846,232 A | 12/1998 | Serbiak et al. | |
| D411,006 S | 6/1999 | Nixon et al. | |
| 6,350,258 B1 * | 2/2002 | Markowiecki | 604/385.01 |
| 6,425,890 B1 * | 7/2002 | Samuelsson et al. | 604/385.17 |
| 6,475,203 B1 * | 11/2002 | Rubio | 604/385.03 |
| 6,613,031 B1 * | 9/2003 | Glasgow et al. | 604/385.03 |
| 6,632,210 B1 * | 10/2003 | Glasgow et al. | 604/385.17 |

* cited by examiner

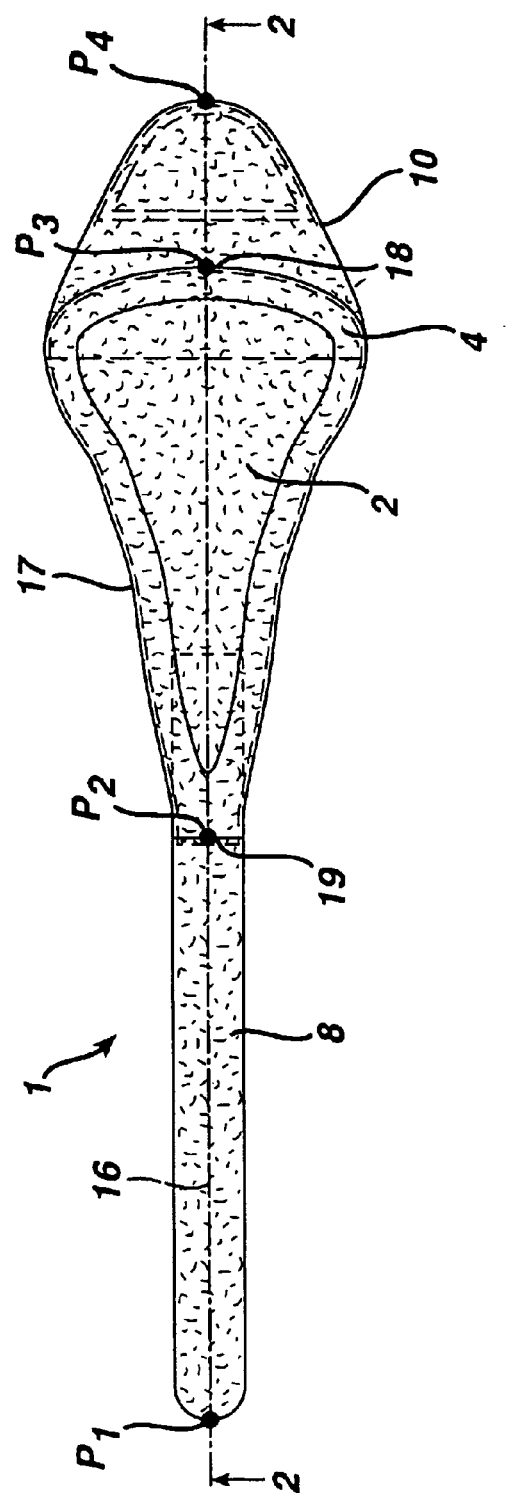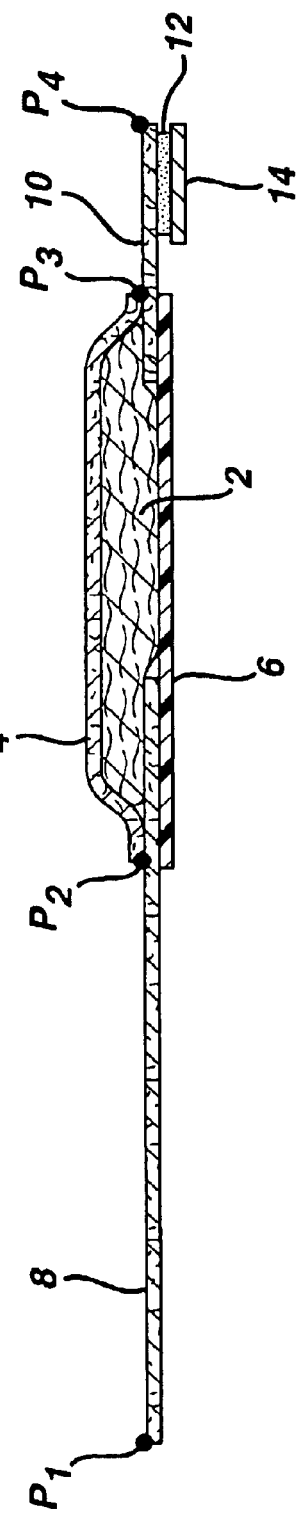

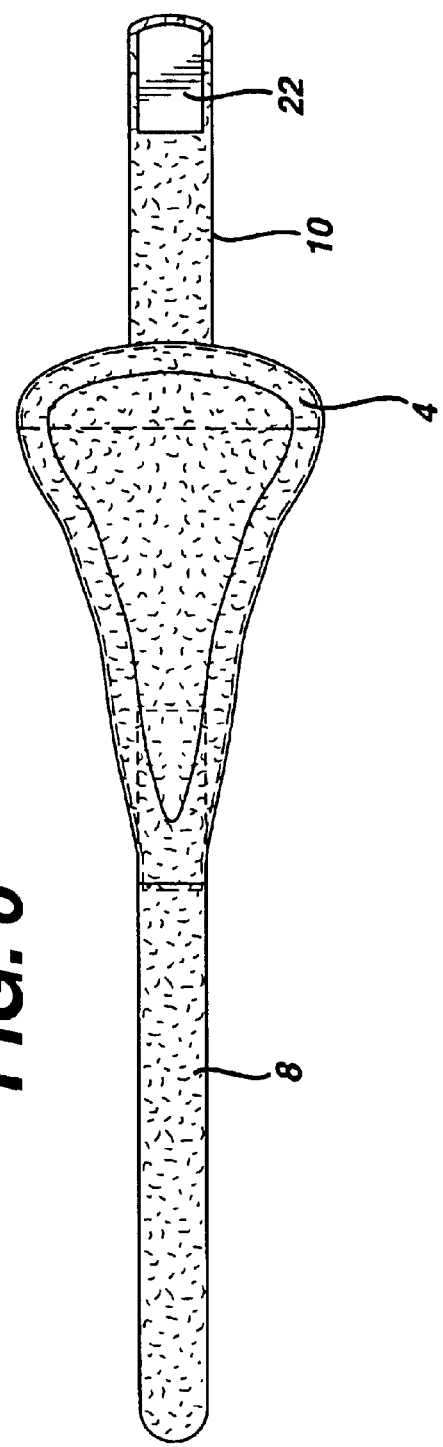
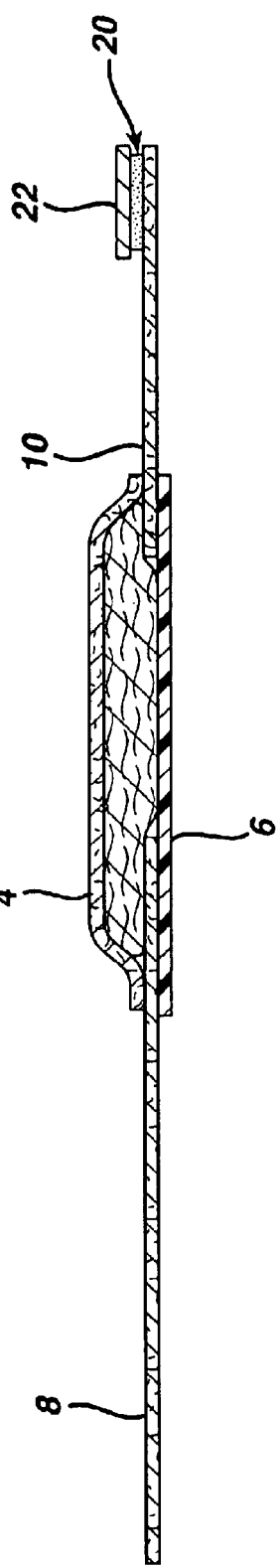
FIG. 6
FIG. 7

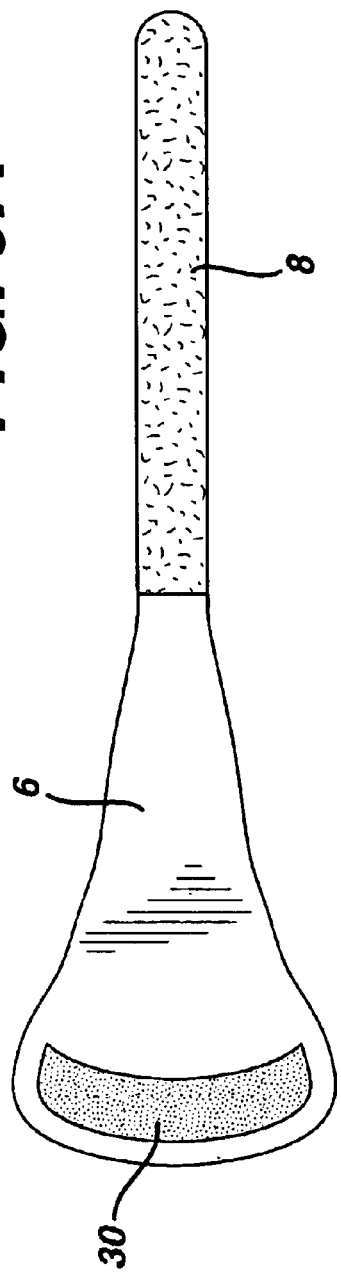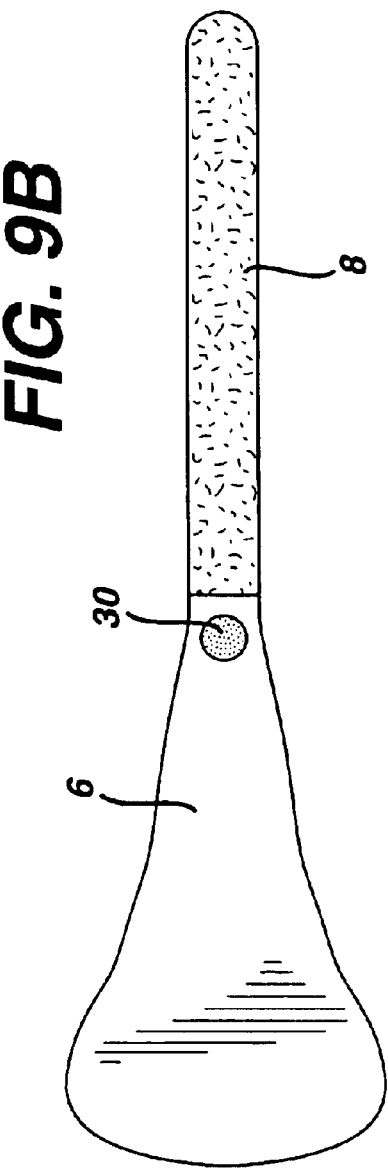

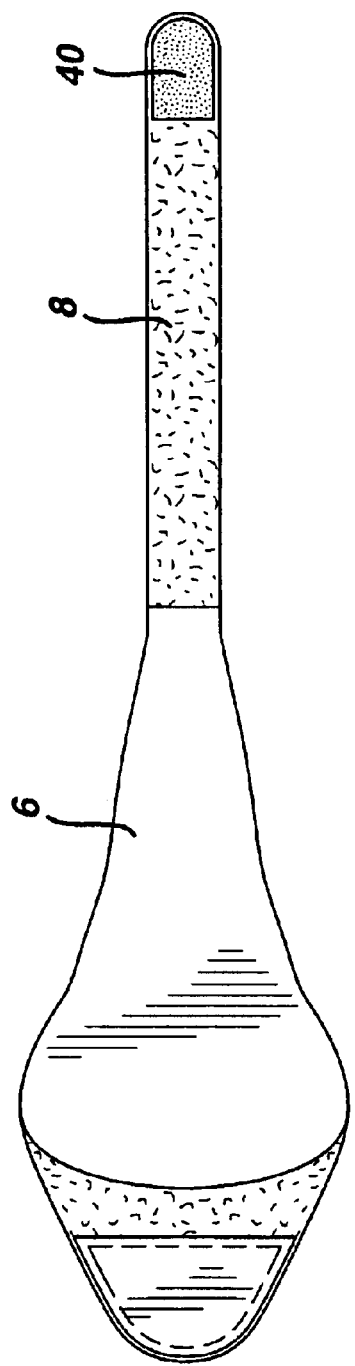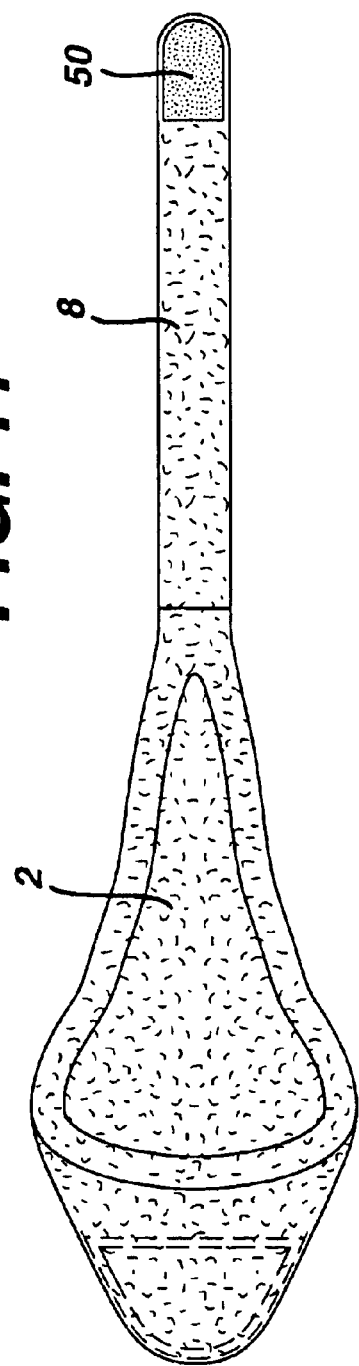

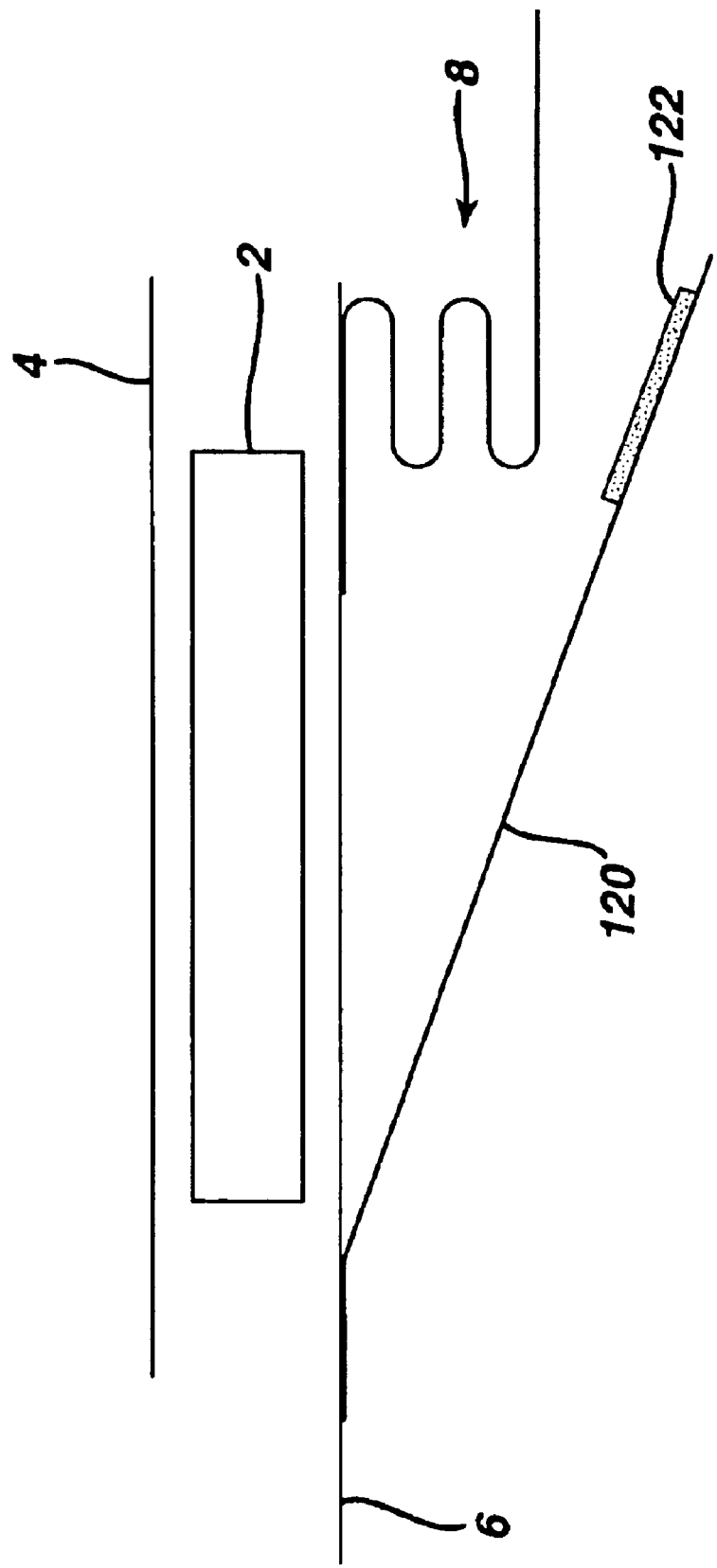

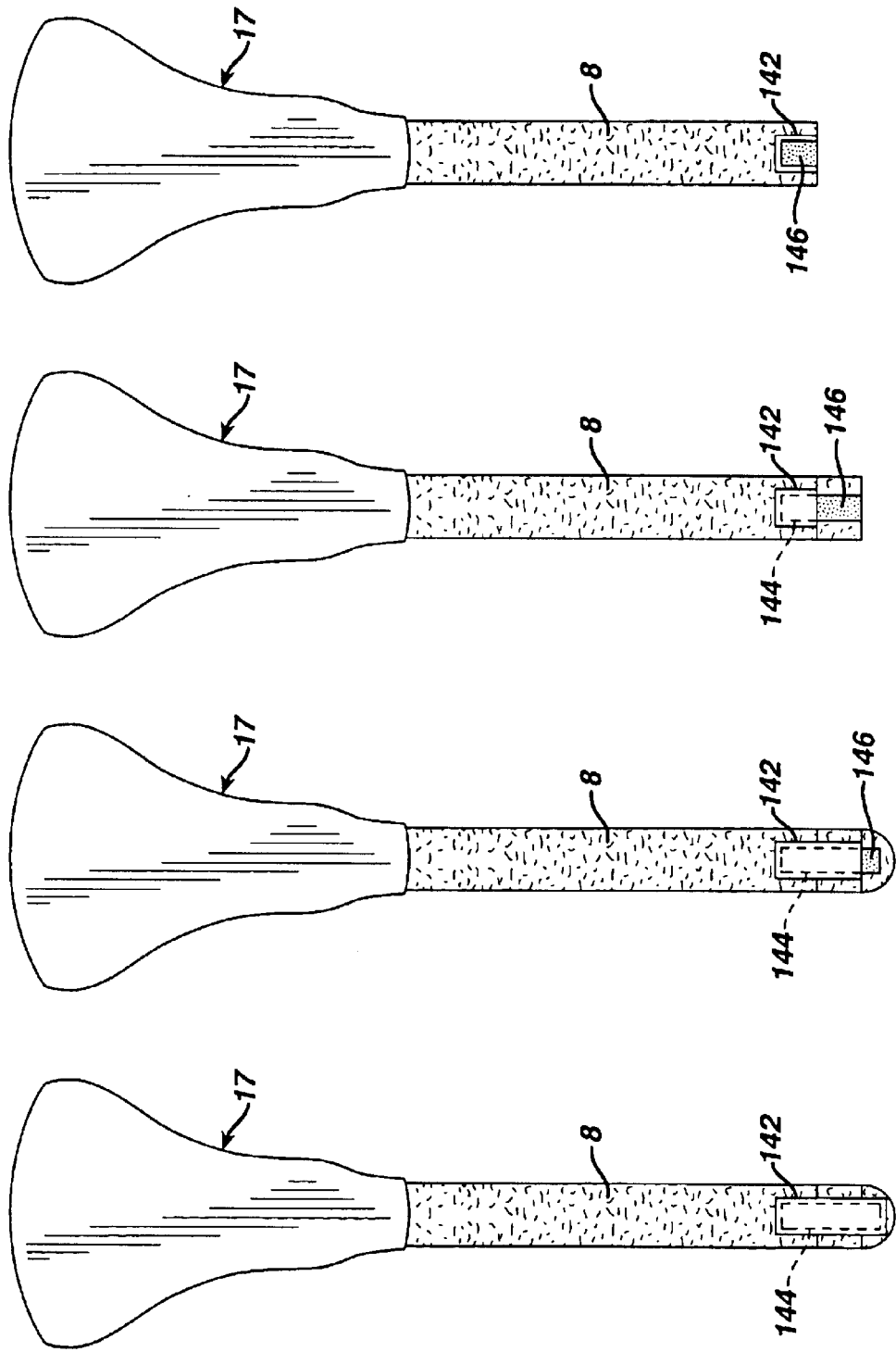

SANITARY NAPKIN WITH ADJUSTABLE LENGTH INTERGLUTEAL STRIP

FIELD OF THE INVENTION

The invention relates to a sanitary napkin having a strip of material that is adapted to extend rearwardly in use to reside in the intergluteal crevice and various means for adjusting the length of this strip.

BACKGROUND OF THE INVENTION

The effectiveness of external feminine sanitary protection products such as sanitary napkins is known to depend upon the proximity of the napkin to the user's perineal area. A close fit allows the napkin to collect fluid near the source of the exit from the body and minimizes fluid traveling along the body. However, despite the importance of fit to sanitary protection, prior art napkins adhesively secured to the crotch of the garment rely on the relatively loose fit of the user's undergarments. Panties worn while menstruating are often older, well-worn garments which fit poorly. New panties, unless specially designed to do so, rarely hold and maintain the napkin close enough to be maintain good body contact. Even specially designed undergarments are deemed by many women to be binding and uncomfortable.

In addition, reliance on adhesive systems that secure sanitary napkins to the undergarment essentially demand that the securing means of the napkin tenaciously adhere to the undergarment at all times. Accordingly, they must resist moisture, sudden torques generated by movements of the body and frictional shearing forces exerted by the movements of the various layers of clothing worn by the user. Not surprisingly, the actual performance of the napkin fails to satisfactorily meet these conditions.

One prior art solution to the fitting problem has been to use sanitary belts to independently support the napkin. Napkins with long tab ends worn with sanitary belts achieve the necessary closeness to the body but are often uncomfortable, inconvenient to use, and cause an indiscreet appearance which women find objectionable. Moreover, belts suspend a napkin in such a way that it is allowed to shift and twist, greatly reducing its effectiveness.

Another solution, contemplated by the prior art, is to attach the product ends to the wearer's skin. Several patents have been directed to devices for collecting body fluids that employ adhesive attachments to the wearer's skin. Zamist, U.S. Pat. No. 3,906,952, is directed to an anatomically contoured sanitary napkin having adhesive patches which attach to the skin of the wearer. These patches have non-disposable, die-cut grippers to receive the ends of the napkin. Levine, U.S. Pat. No. 4,072,151 describes a catamenial napkin having a long, full-sized napkin with adhesive strips on its longitudinal ends for attaching to the wearer's body. Sohn, U.S. Pat. No. 4,484,919, teaches a rectal area dressing for anal incontinence. This rectoperineal device has pressure-sensitive adhesive on an elongated absorbent pad and on extending end members that adhere to the skin surfaces.

While these inventions generally provide a close fit to the wearer's body, many women are adverse to the use of body adhesive. Further these uses of adhesives do not permit stretching in the longitudinal direction to adjust to the wearer's individual sizing needs. Such devices, moreover, are not flexible or resilient enough to allow the pad to move with the body and return to its original position during stooping, bending and twisting. This can lead to uncomfortable binding and twisting of the napkin. Furthermore, the attachment sites of these products, being susceptible to sudden torques and shearing forces, are not always reliable in securing product placement.

The present invention relates to a sanitary napkin whose securing means comprises an intergluteal strip. While use of intergluteal pads has been disclosed in the prior art, their use has been for increased absorbency of fluids present in this area. Examples include U.S. Pat. No. 5,520,675 in the name of Knox-Sigh, U.S. Pat. No. 4,900,319 in the name of Richwine, PCT publication WO 90/04956 in the name of Muller, and U.S. Re. No. 24,385 in the name of Flanders.

The present invention relates to a sanitary napkin whose securing means comprises an intergluteal strip which thereby makes use of the wearer's intergluteal crevice to help secure the napkin to the wearer's body. By using the wearer's body in this manner, the present invention reduces many of the sudden torques and shearing forces associated with the prior art napkins and further provides an improved fit of the sanitary napkin. One problem with the use of this intergluteal strip is that women's anatomical dimensions vary widely as well as widely varying undergarment sizes. Most women do not desire a strip that extends beyond the undergarment and which could be seen by others. Hence, there is a need for an intergluteal strip that can be adjusted in length to fit any woman.

SUMMARY OF THE INVENTION

The invention provides a sanitary napkin which achieves a dynamic body fit. The pad of the napkin is adapted to closely fit to the user's body by means that comprises an intergluteal strip. When the user moves, the user's panty may move, but the napkin stays snugly against the user's body because of this attachment means. The intergluteal strip of the present invention is provided with means for adjusting its length to accommodate women and undergarments of varying sizes.

More specifically, in accordance with one aspect of the invention, there is provided a feminine hygiene pad comprising:

(a) a main pad body having an absorbent core positioned between a cover material and a barrier layer, a rear end which in use is located in proximity to a wearer's buttocks and an opposed front end, a first face adapted to contact with the wearer's body in use and an opposing second face adapted to face toward an undergarment of the wearer in use, a main pad body thickness being defined as the dimension of the main pad body from the first face to the second face, said main pad body adapted to be worn in close proximity to the vagina of the wearer;

(b) said absorbent core being adapted to not significantly extend beyond the anterior portion of the perineum of the wearer in use;

(c) said pad further comprising a substantially planar strip, said strip having a thickness less than the thickness of the main pad body, and said strip extending rearwardly from said rear end of the main pad body, terminating at a distal end and having a length as measured from said rear end of the main pad body to the distal end;

(d) wherein said feminine hygiene pad being configured such that said strip is adapted to be received between the buttocks of the wearer to thereby facilitate retaining said main pad body adjacent to the wearer's vagina in use; and, (e) said feminine hygiene pad further comprising an adjustment means whereby the length of said strip is adjustable by the wearer.

Also provided in accordance with the present invention is a feminine hygiene pad comprising:

(a) a main pad body having an absorbent core positioned between a cover material and a barrier layer, a rear end which in use is located in proximity to a wearer's buttocks and an opposed front end, a first face adapted to contact the wearer's body in use and an opposing second face adapted to face toward an undergarment of the wearer in use, a main pad body thickness being defined as the dimension of the main pad body from the first face to the second face, said main pad body adapted to be worn in close proximity to the vagina of the wearer;

(b) said absorbent core being adapted to not significantly extend beyond the anterior portion of the perineum of the wearer in use;

(c) said opposing second face comprising a strip attachment means;

(d) a substantially planar strip, having a proximal end and a distal end, said strip being releaseably attachable by said strip attachment means to the main pad body, said strip having a thickness less than the thickness of the main pad body, and said strip once attached to said main pad body extending rearwardly from said rear end of the main pad body, terminating at the distal end and having an effective length as measured from said rear end of the main pad body to the distal end;

(e) wherein said feminine hygiene pad being configured such that said strip is adapted to be received between the buttocks of the wearer to thereby facilitate retaining said main pad body adjacent to the wearer's vagina; and, (f) whereby the effective length of the strip is adjustable by the wearer by attaching the strip by said strip attachment means at a point on the strip in between the proximal and distal ends of the strip.

Still further provided in accordance with the present invention is a feminine hygiene pad comprising:

(a) a main pad body having an absorbent core positioned between a cover material and a barrier layer, a rear end which in use is located in proximity to a wearer's buttocks and an opposed front end, a first face adapted to contact with the wearer's body and an opposing second face adapted to face toward an undergarment of the wearer, a main pad body thickness being defined as the dimension of the main pad body from the first face to the second face, said main pad body adapted to be worn in close proximity to the vagina of the wearer;

(b) said absorbent core being adapted to not significantly extend beyond the anterior portion of the perineum of the wearer in use;

(c) said feminine hygiene pad further comprising a substantially planar strip, said strip having a thickness less than the thickness of the main pad body, and said strip extending rearwardly from said rear end of the main pad body, terminating at a distal end and having a length from said rear end of the main pad body to the distal end;

(d) an attachment piece releaseably affixed by a positioning means to said strip at a distance from the distal end selectable by the wearer, thereby establishing an effective length of the strip as measured from said rear end of the main pad body to the attachment piece; and, wherein said feminine hygiene pad being configured such that said strip is adapted to be received between the buttocks of the wearer to thereby facilitate retaining said main pad body adjacent to the wearer's vagina.

These and other features of the invention will be more fully understood by reference to the following drawings

BRIEF DESCRIPTION OF THE DRAWINGS

FIG. 1 is a top view of the inventive pad.

FIG. 2 is a cross sectional view of the pad of FIG. 1.

FIG. 6 is a top view of an alternative embodiment of the invention illustrating a body-adhesive area on the front flap.

FIG. 7 is a cross sectional view of the pad of FIG. 6.

FIGS. 9A and 9B are bottom views of alternative embodiments of the invention in which a garment adhesive area is located on the main pad body.

FIG. 10 is a top view of an alternative embodiment of the invention illustrating a garment-adhesive area on the distal end of the strip for attachment to the rear of the user's panties.

FIG. 11 is a top view of an alternative embodiment of the invention illustrating a body adhesive area on the distal end of the strip for securing the strip to the user's body.

FIG. 13B further depicts the placement of the intergluteal strip in an embodiment of the invention wherein the strip does not contain a stabilizer area, while FIG. 13C depicts the placement of the intergluteal strip in an embodiment in which a stabilizer area is present.

FIG. 21 depicts a side view of an alternative embodiment in which pleats of the strip located between the main pad body and a retaining sheath are used to vary the length of the strip.

FIGS. 27A–7D depict top views illustrating an alternative embodiment having removable sections of the strip where release paper is utilized.

DETAILED DESCRIPTION OF THE INVENTION

Figure 3:
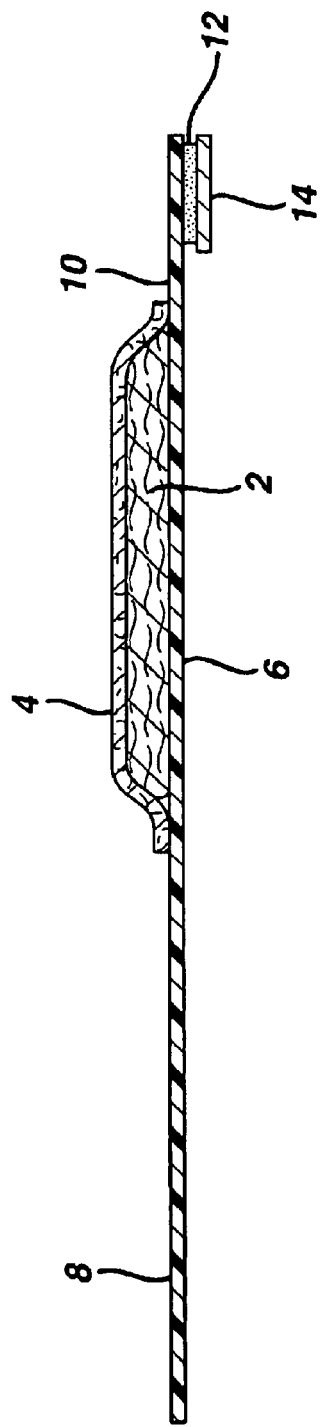
FIG. 3 is a cross sectional view of an alternative embodiment of the invention illustrating the barrier material forming the strip and flap.

During the course of this description, like numbers will be used to identify like elements according to different figures which illustrate the invention.

FIG. 1 shows an embodiment of the present invention and FIG. 2 shows a corresponding cross-sectional view. The depicted feminine hygiene pad is a sanitary napkin 1 having a central longitudinal axis 16. As depicted in these Figs., the main pad body 17 of this sanitary napkin 1 extends from point $P_2$ to point $P_3$ on the longitudinal axis 16 and comprises an absorbent core 2 positioned between a cover material 4 and a barrier layer 6. This main pad body has a front end 18 located adjacent to point $P_3$ and a rear end 19 located adjacent to point $P_2$. In the embodiment shown the cover 4 and barrier 6 are slightly larger than the absorbent system, leaving room to heat seal along the perimeter of the pad.

In the depicted embodiment an intergluteal strip 8 is connected to the main pad body between the cover material 4 and the barrier layer 6 and is preferably located underneath the absorbent core so as not to interfere with absorbency. Construction adhesives as well as heat are exemplary means to attach the strip 8 to the main pad body. In the preferred embodiment the strip is composed of a polyester knit fabric such as that manufactured by Tomen Corporation under the designation AQ 7500. An alternative embodiment the strip may be composed of a nonwoven material which has been microcreped, an example of which being the microcreped material available from Micrex corporation. Use of such a microcreped material allows the material to expand in use to accommodate the user's body. The invention is not limited to these material as alternative materials, to include stretchable or absorbent materials, are contemplated by the inventors.

Moreover, the invention is not limited to positioning of the intergluteal strip between the cover material 4 and the barrier layer 6. An alternative embodiment depicted in FIG. 3 has the barrier layer material itself extended to form both the strip and the optional front flap 10. Alternative embodiments would be having the barrier layer extending to form only one of these appendages while the remaining appendage being an attached material. Accordingly, the materials used in the construction of the strip and or the optional front flap could be selected to best match the desired physical characteristics (e.g. absorbency), to minimize cost, or to simplify construction.

Alternative embodiments (not shown) of the sanitary napkin comprise the presence of embossed channels on the cover material wherein channels are embossed into the cover and absorbent core. Such embossed channels are well known in the sanitary napkin industry.

Figure 4:
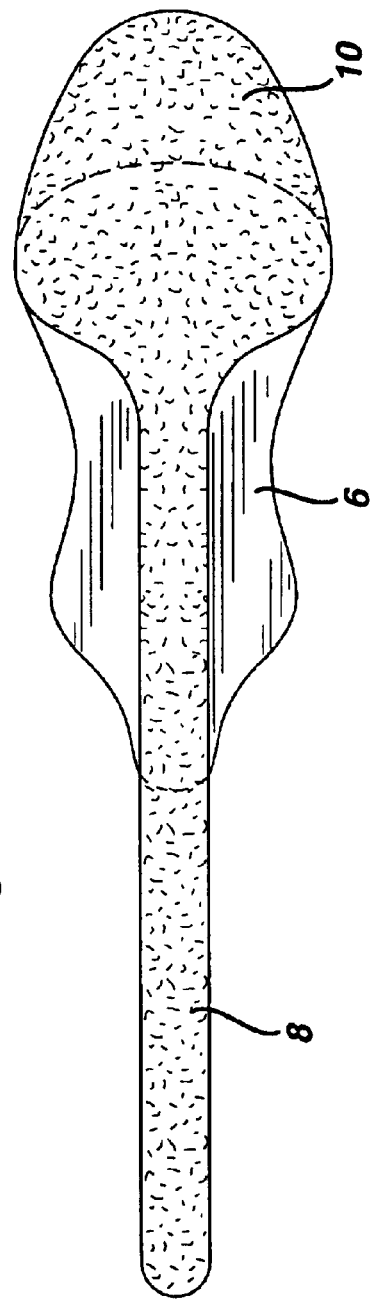
FIG. 4 is a bottom view of another alternative embodiment in which a continuous piece of material, which forms the strip and flap, is attached to the barrier layer.

FIG. 4 shows the garment facing side of an additional alternative embodiment of the invention in which the intergluteal strip 8 and the front flap are one continuous piece of material that has been attached to the barrier layer 6. Construction adhesives as well as heat are exemplary attachment means. In this embodiment construction of the pad is simplified while not limiting the barrier layer to be of the same material as that of both appendages.

As depicted in FIG. 2 the optional front flap 10, located at the front end 18 of the main pad body 17, comprises positioning adhesive 12 and release paper 14 on the garment-facing side. In the preferred embodiment depicted in FIGS. 1 and 2, the front flap is sandwiched between the cover 4 and barrier 6, and is attached using construction adhesive as well as heat. In this preferred embodiment it is envisioned that this front flap is constructed of a stretchable material to aid in both comfort and fit of the pad.

Figure 5:
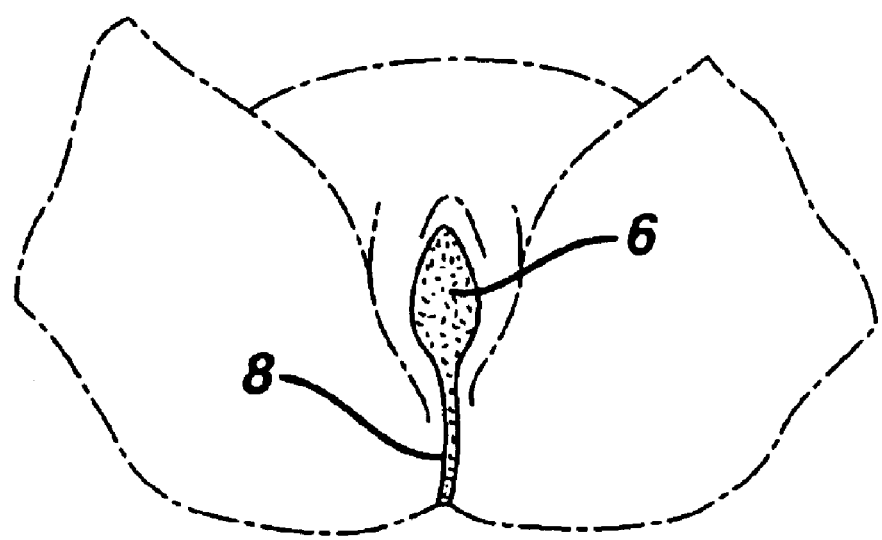
FIG. 5 is a front view of the inventive pad as worn by a wearer.

As illustrated in FIG. 5 the intergluteal strip extends rearwardly between the buttocks of the wearer. The placement of the intergluteal strip in this position provides an additional anchoring means for the pad. It is considered an important feature of the present invention that in use, the absorbent core 2 of the pad does not extend significantly beyond the anterior portion of the user's perineum. As is well known, the perineum of a user is defined to be that area that extends between the anus and the posterior part of the external genitalia. Consequently, in normal use the absorbent core of the pad does not rearwardly extend significantly beyond the user's anus, and accordingly extends minimally, if at all, into the intergluteal crevice of the user. Preferably, when the pad is worn, the absorbent core extends less than 25 mm beyond the anterior portion of the user's perineum; and most preferably does not extend beyond the anterior portion of the user's perineum.

In the preferred embodiment of the present invention the sanitary pad of the present invention provides dynamic fit by anchoring the front end of the pad to the body through the use of just one attachment point to the panty. The pad is draped closely to the body through the use of the intergluteal strip. Once in place, the pad moves with the body, not with the panty. Hence, dynamic fit is achieved. Because of this optimal fit, the user can achieve the same protection in a smaller, more discreet pad.

Alternative embodiments utilize a body adhesive to secure the front end of a body-facing side of the pad without the necessity of attaching it to the user's panty. As used herein, the terminology "body adhesive" refers to a low tack adhesive that is capable of maintaining adhesive contact between a wearer and the pad and which permits easy removal of the pad without undue discomfort to the wearer. Body adhesives are known in the art, and the particular choice of a body adhesive is not, per se, critical to the invention, provided of course provides the above described capabilities. In the embodiments depicted in FIGS. 6 and 7, the front flap 10 is of sufficient length such that when worn, the body adhesive area 20 of the flap extends above and hence is not in contact with the pubic hair area of the user.

Figure 8:
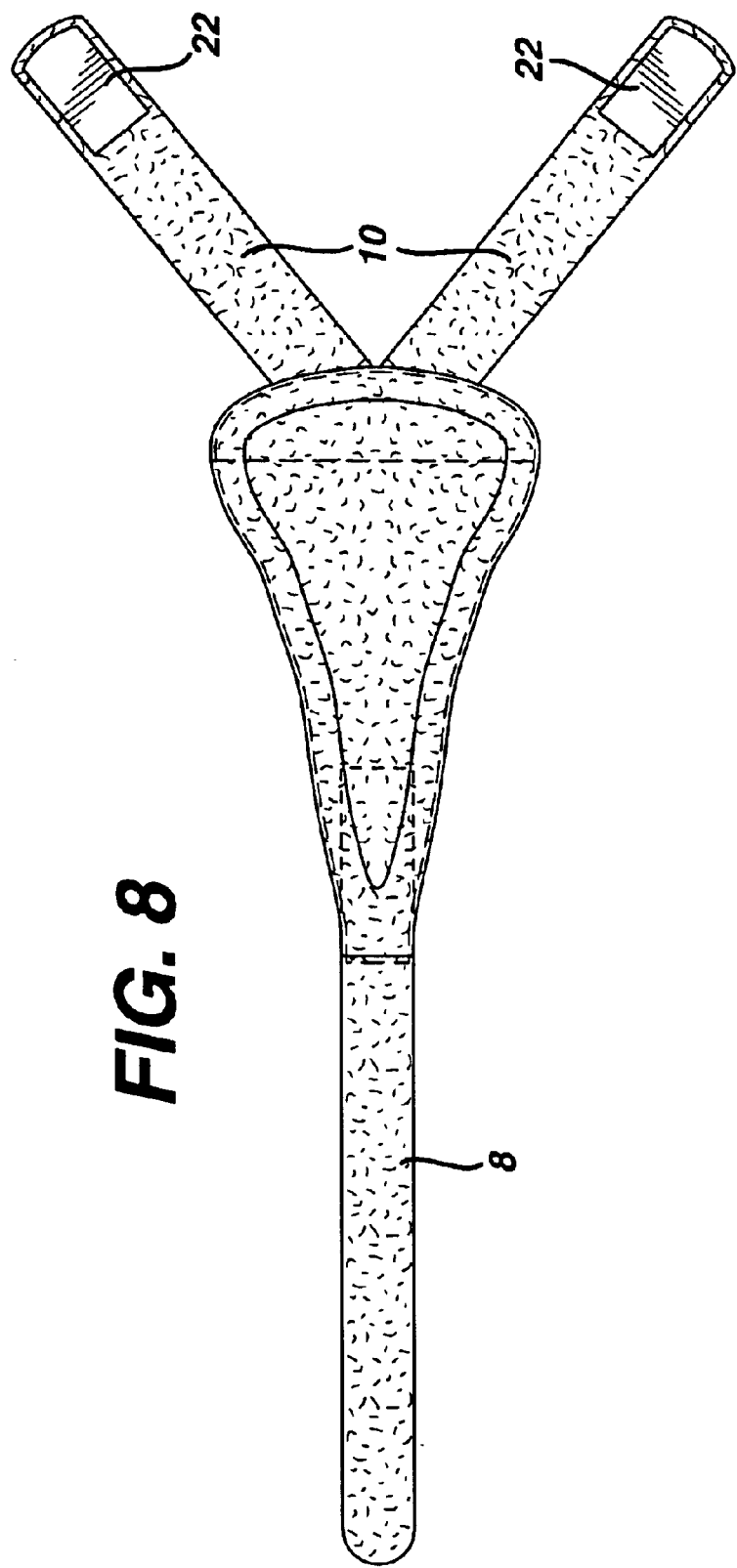
FIG. 8 is a top view of an alternative embodiment of the invention illustrating a dual front flap arrangement having a body-adhesive area on each front flap.

As depicted in FIG. 7 this adhesive area is covered by release paper 22 prior to its use. An alternative embodiment of this aspect of the invention is depicted in FIG. 8 in which two front flaps are utilized to form the pad into a "Y" shape. Consequently when worn, the ends of the flaps extend both up and away from the user's crotch area to avoid contact of the body adhesive with pubic hair area.

FIG. 9A depicts yet another alternative pad in which the body of the pad is secured to the user's undergarment by use of a positioning adhesive area 30 on the barrier layer and hence on the garment facing side of the pad. Consequently, the front flap is not required.

An alternative use of garment adhesive is shown in FIG. 9B. This figure depicts a smaller position adhesive area 30 that is located near the strip. This adhesive area is used chiefly to help properly position the pad in the wearer's undergarment just prior to use. Once the undergarment is pulled up into a wearing position and the strip 8 is placed in the intergluteal crevice; it is contemplated that this adhesive area would no longer secure the pad to the user's undergarment.

In the preferred embodiment, the strip is substantially free of adhesive on its distal end. As illustrated in FIG. 5 the intergluteal strip is placed by the wearer in her intergluteal crevice. This mere positioning of the strip into this area has been found to sufficiently secure the strip end of the pad to the wearer. Alternative embodiments are contemplated in which the intergluteal strip is of sufficient length to employ an adhesive on its distal end. As depicted in FIG. 10 this adhesive area 40 may be positioned on the garment facing side for attachment to the user's undergarment. Alternatively a body adhesive area 50 on the body facing side could be employed for securing the distal end of the strip as depicted in FIG. 11. The distal end of the intergluteal strip can have such adhesives in a range of patterns, including full coverage of the strip contour, strips, dots, or other. A napkin containing such adhesive areas would preferably utilize an adhesive release paper to facilitate packaging and handling of the napkin prior to its use.

In the following discussion length measures correspond to distances along the central longitudinal axis 16 of the pad as depicted in FIG. 1 and width measures relate to distances along a corresponding horizontal axis perpendicular to this longitudinal axis. Accordingly, the length of the intergluteal strip 8 is the distance from point $P_1$ to point $P_2$ along longitudinal axis 16. Similarly, the main body of the pad extends in length from point $P_2$ to point $P_3$ along this axis. And finally, the length of the front flap is the measure from point $P_3$ to point $P_4$.

In the preferred embodiment the front flap has a rounded shape that flows from the contours of the main pad body as depicted in FIG. 1. Its width varies along the length of the flap. The widest portion is adjacent to the main pad body and the narrowest portion is at the distal end, ending in a rounded point. The widest portion has a width of 7 cm, but can vary with the width of the main pad body, from 7 to 10 cm. The length of the flap extends 4 cm beyond the end of the main pad body. The length of the flap can range from 3 to 7 cm.

The strip extends from the rear end 19 of the main pad body. The width of the strip can vary from 0.5 to 2.5 cm. Preferably, the strip has a width of 1.5 to 2 cm. The thickness of the strip is preferable less than 1 cm and most preferably less than 5 mm. This thickness range is an important feature of the present invention as it relates to the user's comfort.

In the preferred embodiment the main body of the pad is adapted to be worn outside of and in close proximity to the vagina of a wearer. Accordingly, in this embodiment the main pad body is substantially planar on its body facing side. Additional embodiments, while also substantially planar, have some taper in a front to back direction, or in a side to side direction, or both. However, the invention is not limited to being worn outside of the vagina. Additional alternative embodiments are contemplated in which the main pad body comprises a raised area for insertion into the vagina. Such an interlabial feature yields several advantages to include aiding in proper positioning of the pad and/or permitting a concentration of absorbent materials at the fluid discharge location.

In the preferred embodiment of the present invention, the absorbent core is of sufficient length to only cover the length of the user's labia, that is, it is in the range 8.0 to 13.1 cm in length. The length of the main pad body is preferably greater than the length of the absorbent core 2, so that a perimeter of barrier layer 6 and cover material 4 surrounds the absorbent core. The width of the perimeter can range from 0.5 to 2 cm. This means the length of the main pad body can range from 9.0 to 17.1 cm. Most preferably, the width of the perimeter is 1 cm. With a most preferred length of absorbent body of 11.5 cm, this means that the most preferable length of the main pad body is 13.5 cm.

The width of the main pad body most preferably varies along the length, becoming narrower at the rear end 19 of the main pad body. It could be relatively constant in width as well. In the preferred embodiment with a variable width, the maximum width occurs near the front end 18. The width there is in the range 8 cm to 10 cm. In the preferred embodiment, the main pad body is most narrow, at the rear end 19 near the strip to thereby provide a more comfortable fit. Accordingly, this width is preferably between 0.5 and 4 cm. Most preferably, this width is 2 cm. Further, in the preferred embodiment the narrowest part of the main pad body should approximately equal the width of the intergluteal strip 8, which can vary from 0.5 to 2.5 cm.

In accordance with alternative embodiments the present invention relates to full size napkins wherein the main pad body has a length of 200 cm to 250 cm and overnight napkins whose main pad body has a length of 250 cm to 350 cm. In addition, alternative embodiments are contemplated in which the napkin has one or more wings extending from each lateral side of the main pad body, these wings to be used to further secure the napkin to the user's undergarments. Such wings are well known in the sanitary napkin industry.

Figure 12A:
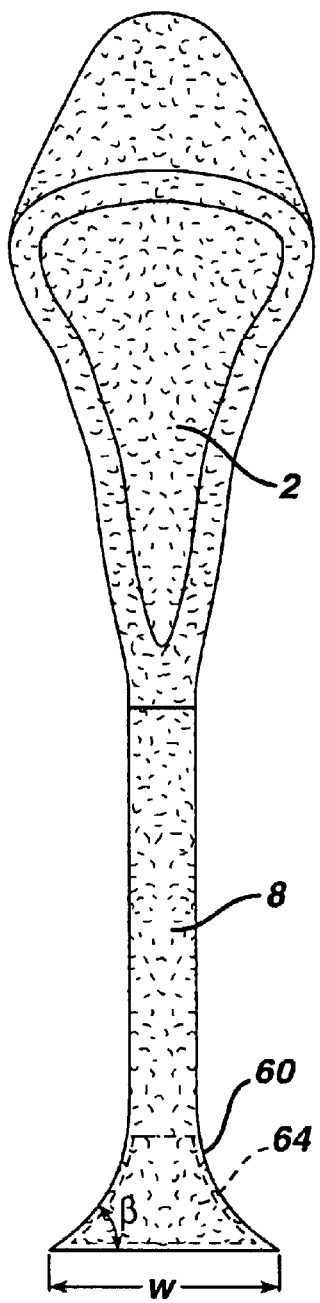
FIGS. 12A and 12B illustrate alternative embodiments of the invention in which a stabilizer area of the strip is depicted.
Figure 12B:
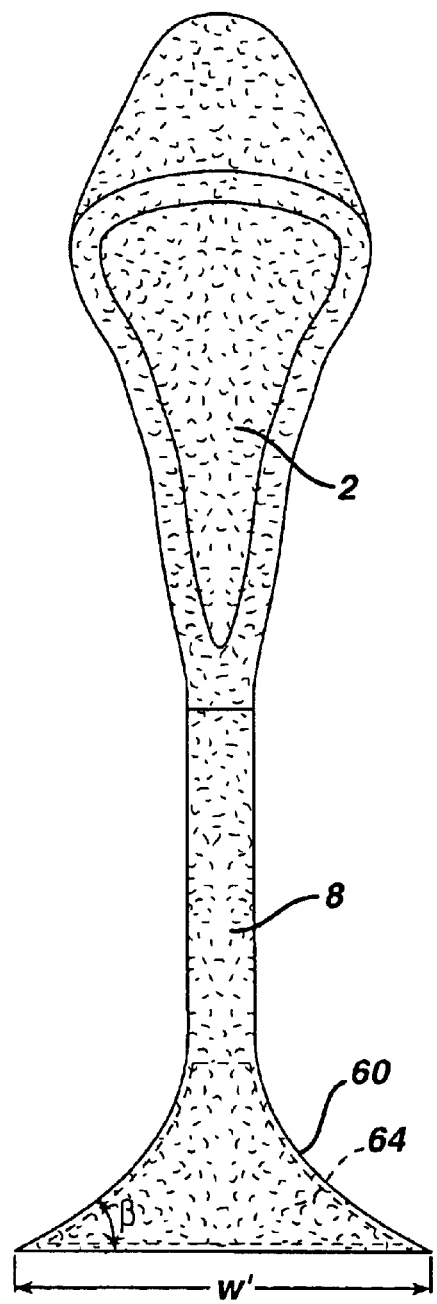

Additional embodiments of invention relate to a widened distal end of the strip thereby forming a stabilizer area 60 of the strip. FIGS. 12A and 12B depict alternative embodiments of this invention in which the width (w and w', respectively) of the stabilizer area 60 is greater than the width of the intergluteal strip 8. This arrangement helps stabilize the strip by providing a larger attachment area that distributes the forces acting upon the strip by spreading them laterally. As illustrated in these figures, both the width of the stabilizer portion, and the angle of stabilization, $\beta$, combine to determine the surface area of the stabilizer area 60.

This stabilizing area may contain an area of adhesive 64. In the preferred embodiment this adhesive would be covered by a release paper (not shown) prior to use. In FIGS. 12 panty adhesive is depicted on the garment facing side of the strip. In the preferred embodiment body adhesive, for directly attaching the strip to the user's body, would be utilized. Moreover, while FIGS. 12A and 12B illustrate the adhesive area essentially taking the same shape as the stabilizing area, this is not required. Any number of adhesive pattern area shapes, including but not limited to, square, rectangular, circular, or even linear are contemplated by the invention.

Figure 13A:
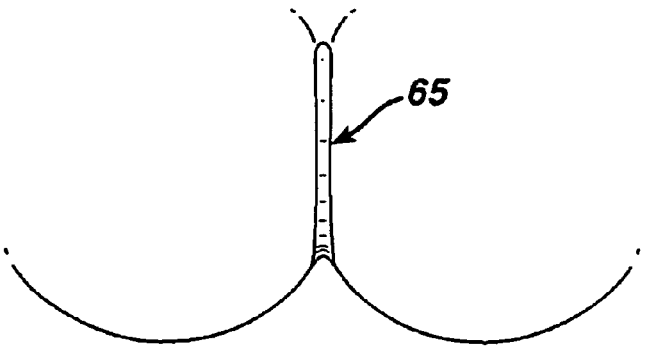
FIGS. 13A, 13B and 13C depict a rear view of a user's buttocks and the intergluteal crevice therein.
Figure 13B:
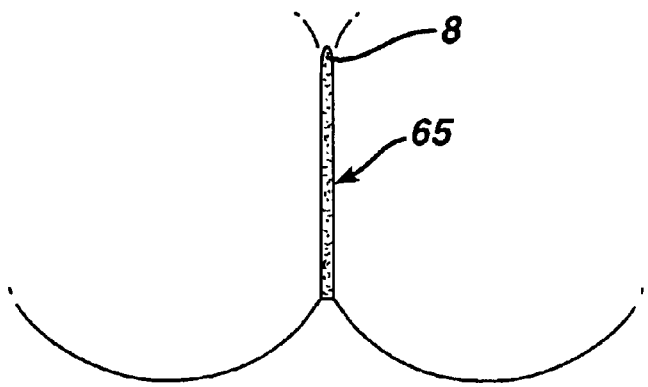
Figure 13C:
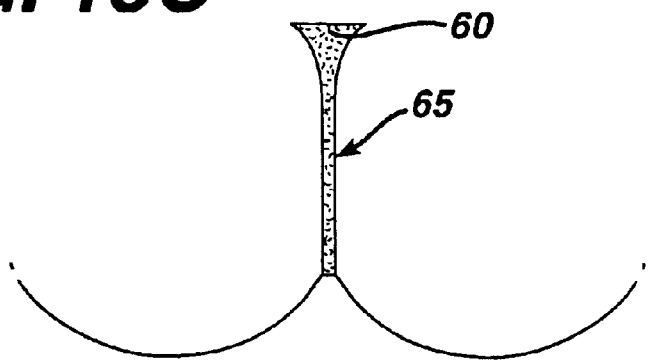

FIGS. 13A, B and C each depict a rear view of a user's buttocks. FIG. 13A illustrates the user's intergluteal crevice 65. FIG. 13B depicts an intergluteal strip 8, which lacks a stabilizing area, positioned in the intergluteal crevice 65. FIG. 13C illustrates a user wearing an intergluteal strip 8 having a stabilizing area 60. Such a stabilizing area not only stabilizes the forces acting upon the strip, but also helps prevent the strip from residing too far in the intergluteal crevice, a situation which users may find uncomfortable.

FIG. 13C further illustrates how the width of the stabilizer area, W, and the angle of stabilization, β, combine to effect the surface area of the stabilizer area. The lower limits of these parameters are influenced by the stability of the material used. The upper limits of these parameters are influenced by discretion since, as illustrated in FIG. 13C, the stabilizer area resides outside of the intergluteal crevice when the strip is in position. In the preferred embodiment the angle of stabilization, β, can range from 5° to 80°. While for a 20 mm wide strip, the preferred range of w is from 30 to 120 mm.

Figure 14:
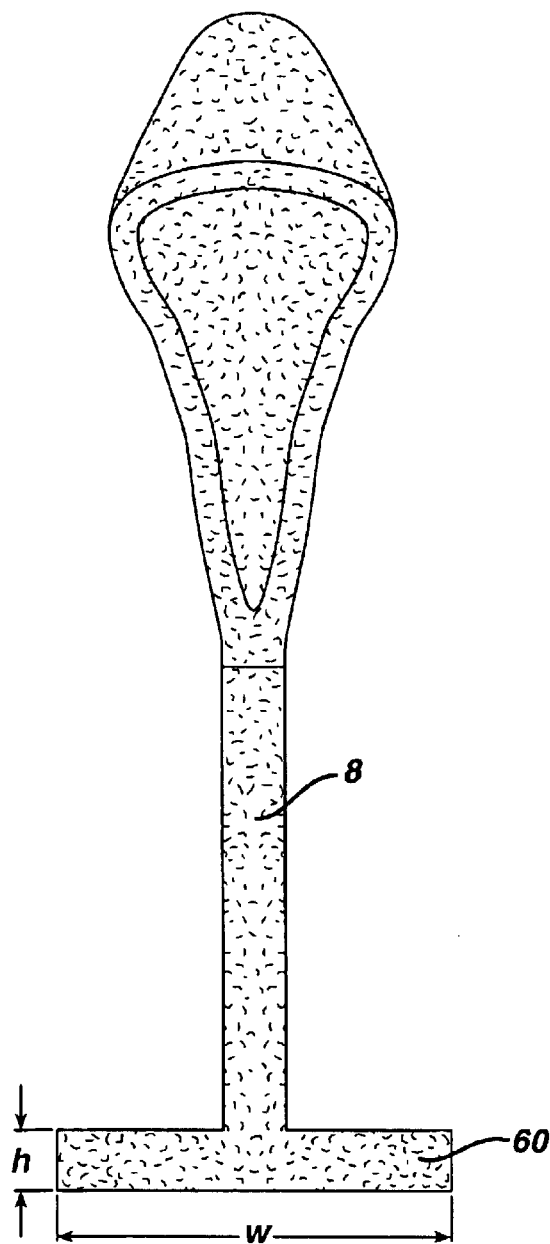
FIGS. 14 and 15 depict alternative embodiments of the invention wherein the stabilizer area has alternative shapes.
Figure 15:
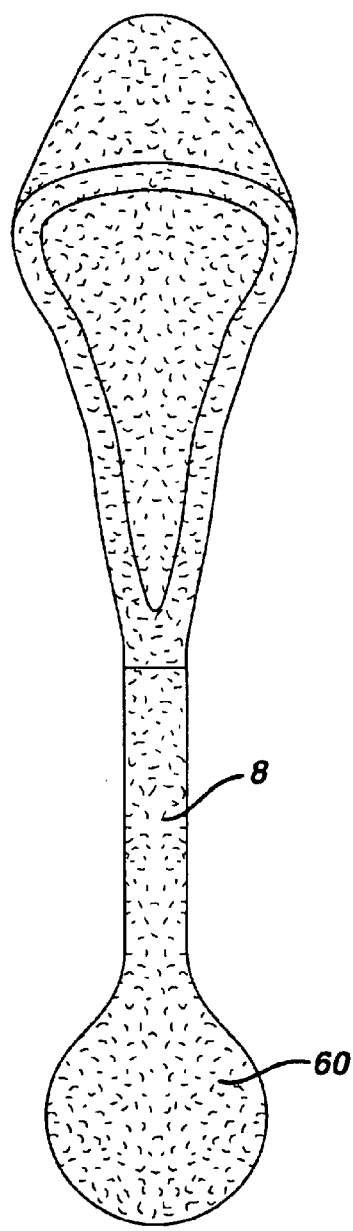

FIG. 14 depicts an alternative embodiment of the stabilizer area 60. In this embodiment, the height, h, preferentially ranges from 6 mm to 40 mm and for a 20 mm wide strip, the width, w, preferentially ranges from 30 to 120 mm. FIG. 15 depicts yet another alternative embodiment of the shape of the stabilizer area 60. The invention is not limited to these illustrated shapes as any non-insignificant widening of the distal end of the intergluteal strip 8 will perform as a stabilization area and help prevent the strip from residing too far in the intergluteal crevice.

Further, in situations in which an adhesive is desired at the distal end of the intergluteal strip, this stabilizing area provides an increased surface area upon which such adhesive can be placed. Finally, the stabilization area provides a convenient tab to aid the wearer in the placement of the strip at time of use.

The above discussion of the stabilization area relates primarily to that area being a widening of the strip material at the distal end of the strip. The invention is not limited in this regard as it is contemplated that a separate stabilizing strip of material can be attached to the distal end of the intergluteal strip to thereby form the stabilization area. In the preferred embodiment this stabilizing strip would be readily stretchable. Non-limiting examples of suitable materials include fabrics formed from elastane fibers such as segmented polyurethane and are commercially available under the tradename LYCRA which is manufactured by the DuPont Corporation; AQ 3005, a polyester/polyurethane knit laminate, and AQ 7500, a polyester knit fabric, both commercially available from the Tomen Corporation; FAB-RIFLEX 102, a laminate of PP nonwoven and a high stretch elastic film, manufactured by Tredagar Corporation; and a cotton/rayon bandage material, with the yarns mechanically twisted to provide stretch available from Conco under the trade designation ARTICLE 207.

As noted above the present invention provides an intergluteal strip to help retain a sanitary napkin snugly against a woman's body. One potential problem with such a strip is that women's anatomy differs widely, particularly in a posterior region. In addition, different size and style undergarments are commonly worn during menstruation and most women, in the interest of discretion, do not desire a strip that extends beyond their undergarment. An important feature of the present invention is that it permits the length of the intergluteal strip to be adjusted to address this problem. Further, the alternative embodiments depicting these various adjustment means do not require a strip composed of an elastic material thereby providing greater comfort to the user.

Figure 16A:
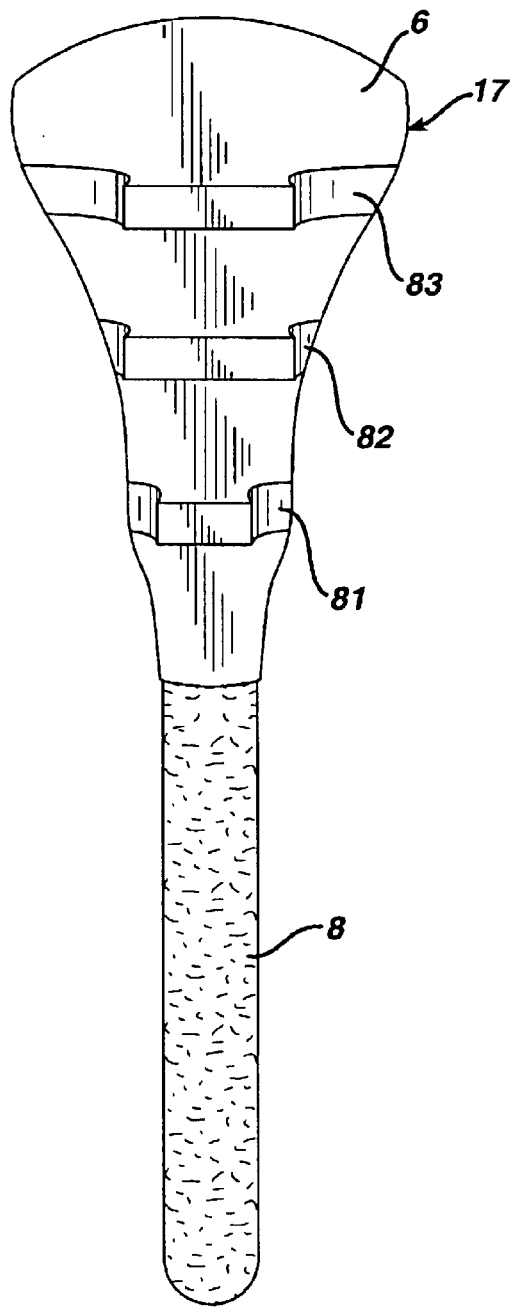
FIGS. 16A and 16B depict a top view of an alternative embodiment in which loops on the main pad body are used to vary the length of the strip.
Figure 16B:
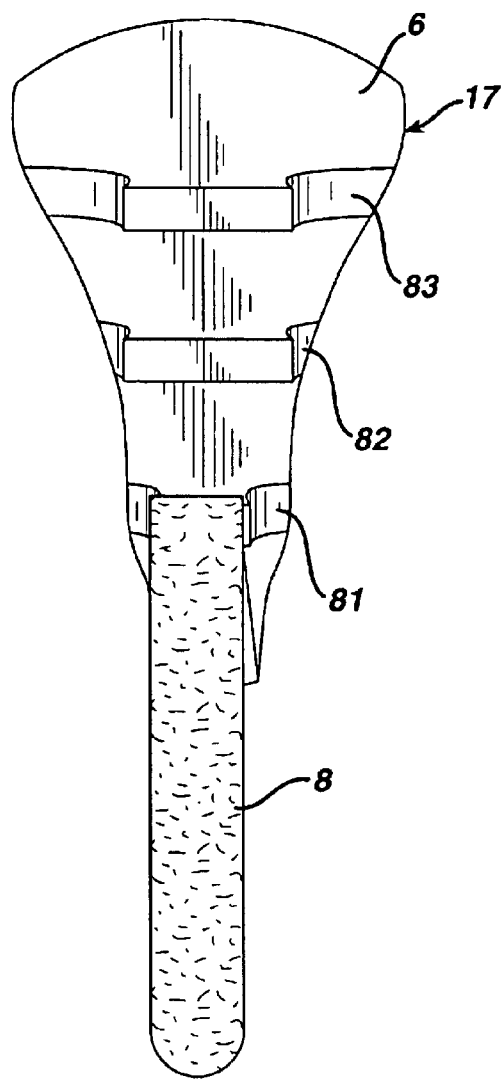

FIG. 16 depicts an embodiment wherein the adjustability of the intergluteal strip is attained by the use of alternative "rungs of a ladder." In FIG. 16A the garment-facing surface, i.e., the barrier layer 6, of the main pad body 17 is shown in plan view. As depicted in this drawing, the intergluteal strip 8 is attached to the main pad body 17 and is not looped through any of the ladder rungs (items 81, 82 and 83). In FIG. 16B the intergluteal strip 8 is looped through the bottom ladder rung 81. This shortens the effective length of the intergluteal strip, making it fit smaller sized undergarments and/or smaller sized women. Alternatively, the intergluteal strip 8 could be looped through the middle 82 or the top 83 ladder making the effective length of the intergluteal strip increasingly shorter. Alternative embodiments are contemplated in which more or less rungs are utilized.

In alternative embodiments the "rungs of the ladder" can vary in size and quantity. The number of rungs is dictated by their size, spacing, and the size of the pad. In the preferred embodiment, a 135 mm long pad has 3 rungs of 0.8 cm length, spaced 2.2 cm apart. For a 135 mm long pad, 3 or 4 rungs 0.8 to 3 cm in length, spaced 1 to 4 cm apart work well. The number of rungs needed is also dictated by the strip length. For a 170 mm strip that is tucked and sealed inside the pad, making an effective length of 150 mm, one rung should suffice. As the length of the strip increases, the optimal number of rungs increases. Therefore, for a strip of effective length of 265 mm on a 135 mm long pad, the optimal number of rungs is preferably 3 or 4, again depending on the size and spacing of the rungs.

The rungs are composed of the same material as the film backing or barrier layer 6 so that they are easily heat sealed at the edges to the sides of the pad. Other materials would work as well, as long as they are easily and permanently attached with heat or adhesive.

FIG. 17 depicts an alternative embodiment in which an attachment piece is used to adjust the effective length of the intergluteal strip. FIG. 17A is a plan view of the garment-facing surface, i.e., the barrier layer 6, of the main pad body 17 and intergluteal strip 8. A VELCRO loop material 85 is depicted as covering almost half the length of the intergluteal strip 8. FIGS. 17B and 17C show the plan view of the garment-facing side and the body-facing side, respectively, of the attachment piece 87. A VELCRO hook and loop fastening material 89 is contained on the body-facing side and an adhesive patch 91 is positioned on the garment-facing side.

Figure 17A:
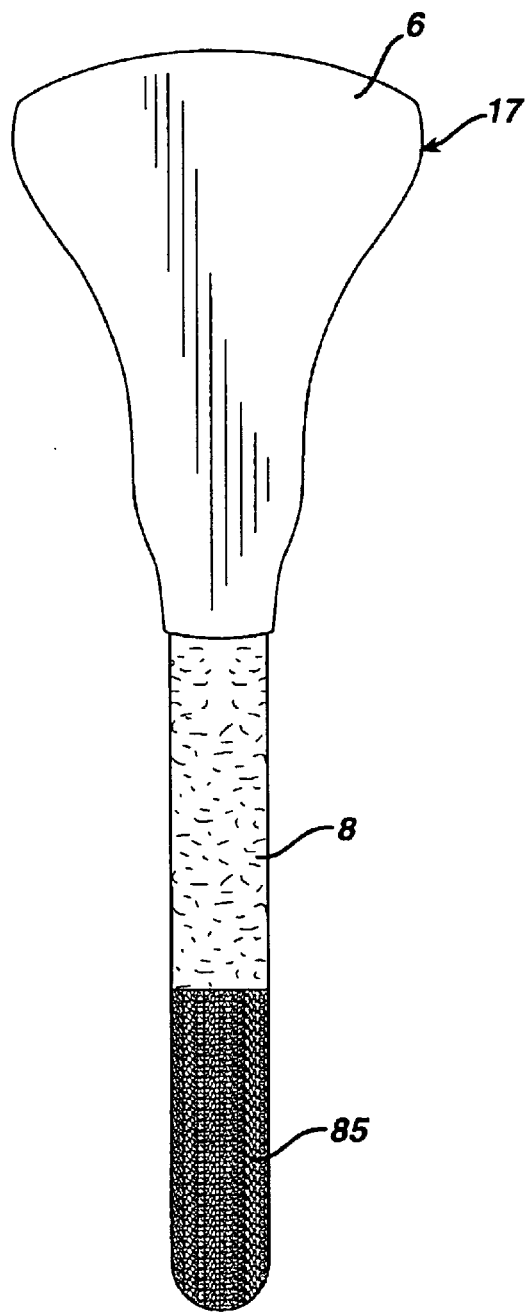
FIGS. 17A–17E depict a top view of an alternative embodiment in which an attachment piece is variably located along the length of the strip and secured by VELCRO.
Figure 17B:
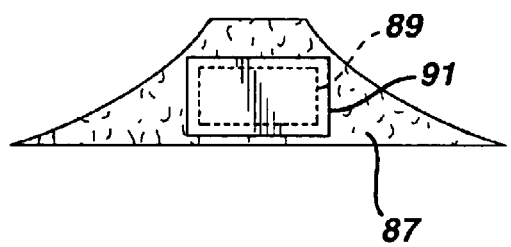
Figure 17C:
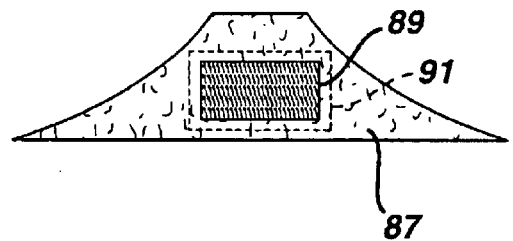
Figure 17D:
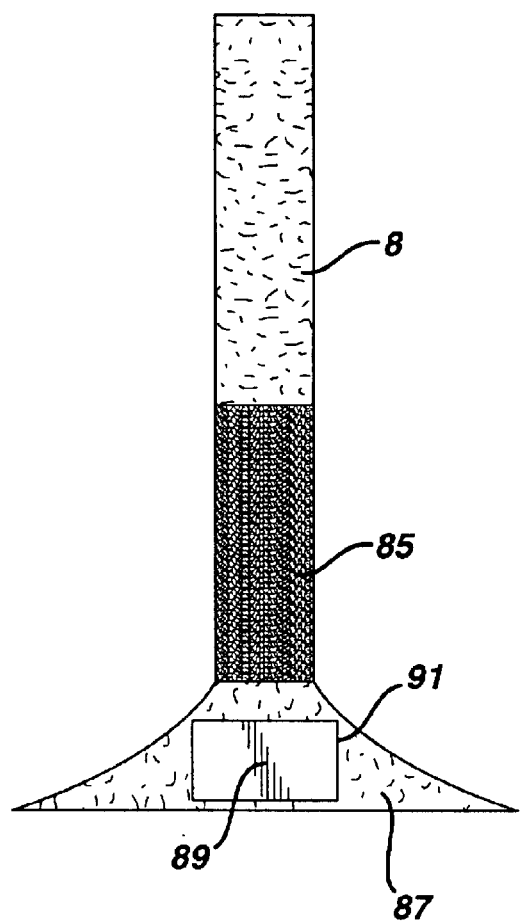
Figure 17E:
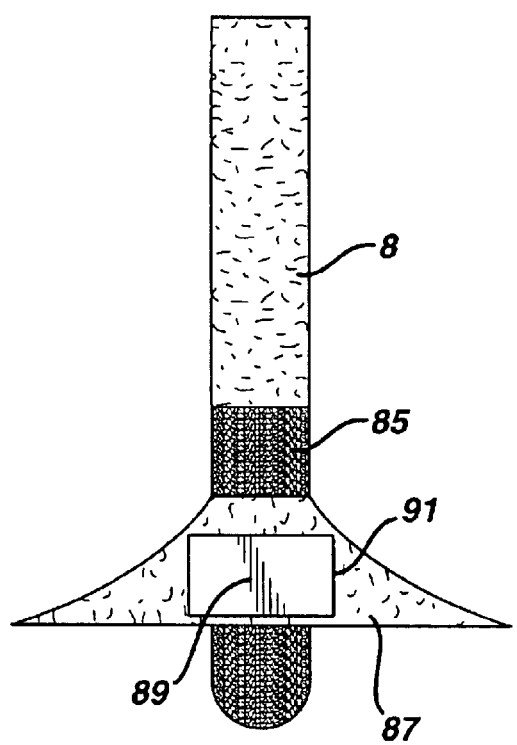

FIGS. 17D and 17E depict how this arrangement of materials is utilized to adjust the effective length of the intergluteal strip 8. In FIG. 17D the attachment piece 87 is positioned at the distal end of the intergluteal strip 8, to thereby provide the longest possible effective length of the strip by maximizing the point at which the strip attaches to the undergarment. In FIG. 17E the attachment piece 87 is positioned at a midpoint along the VELCRO hook and loop fastening material 85, thereby shortening the effective length of the intergluteal strip 8. Thus, this embodiment of the invention provides for adjustability of the intergluteal strip's effective length by placement of the attachment piece at a variable position along the intergluteal strip. This allows the user to shorten the intergluteal strip to the desired effective length.

As noted above, the VELCRO coverage of the intergluteal strip 8 is approximately 50%. This coverage can range from 25% to 75%, with a tradeoff between comfort and adjustability. That is, greater coverage yields greater adjustability but also results in less comfort due to the stiffer VELCRO. Since the VELCRO loop material is less stiff than the VELCRO hook material, it is optimal to have the VELCRO loop material on the intergluteal strip 8. However, the VELCRO hook material could be positioned there as well. Additionally, the VELCRO hook material could be replaced by a thin terrycloth material or similar "grabby" material to attach to the VELCRO loop material. Similarly, other hook and loop type fastening systems can be used.

FIGS. 18 depicts an alternative embodiment wherein the adjustability of the intergluteal strip is attained by utilizing an attachment piece having cohesive adhesive. FIG. 18A shows the garment-facing side of the main pad body 17 and the intergluteal strip 8 in plan view. There is cohesive adhesive 93 covering almost half the distance of the intergluteal strip 8. FIGS. 18B and 18C show the plan view of the garment-facing side and body-facing side, respectively, of the attachment piece 87. An additional cohesive adhesive 95 area is placed on the body-facing side and an adhesive patch 91 is on the garment-facing side of this attachment piece 87.

Figure 18A:
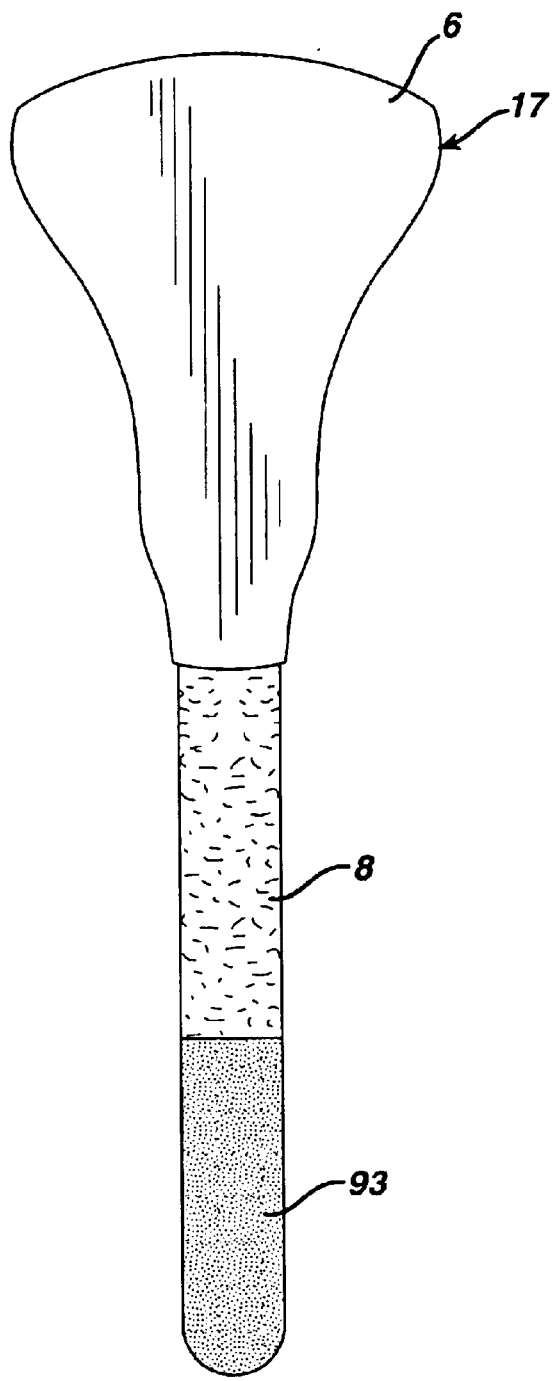
FIGS. 18A–18E depict a top view of an alternative embodiment in which an attachment piece is variably located along the length of the strip and secured by cohesive adhesive.
Figure 18B:
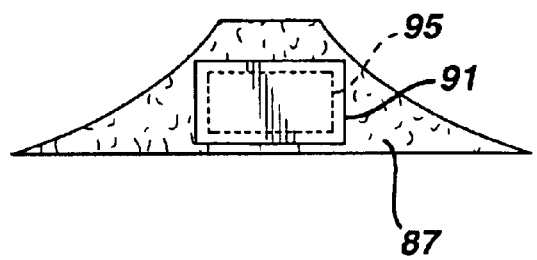
Figure 18C:
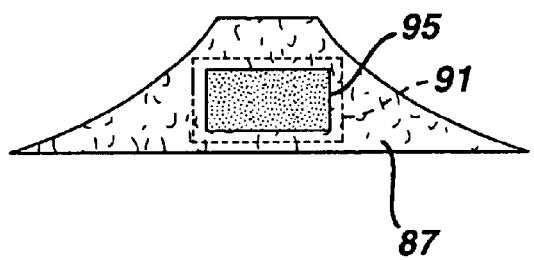
Figure 18D:
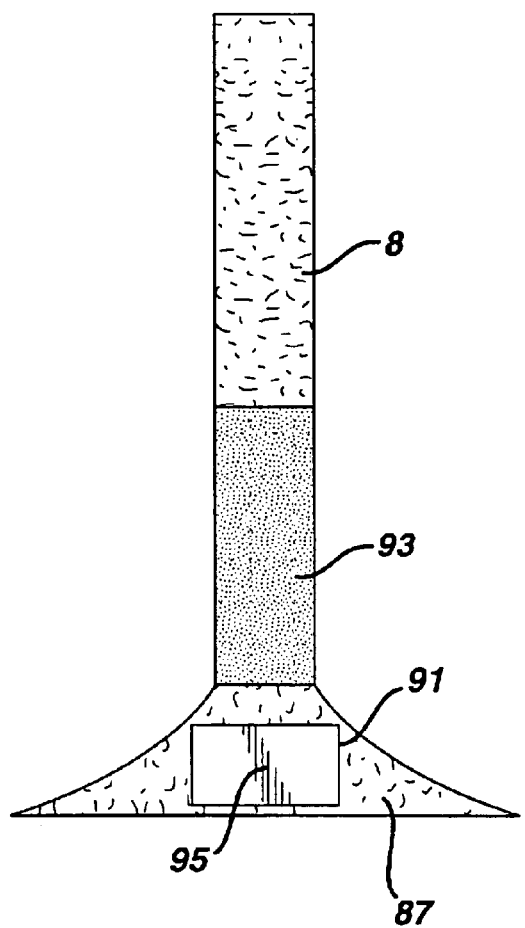
Figure 18E:
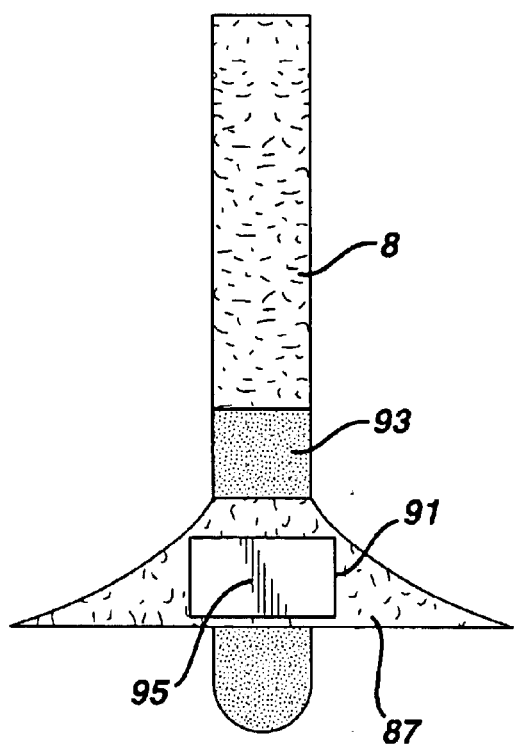

In FIG. 18D, the attachment piece 87 is positioned at the distal end of the intergluteal strip 8, to provide the longest possible strip attaching to the undergarment. In FIG. 18E, the attachment piece 87 is positioned at a midpoint along the cohesive adhesive 93, thereby shortening the effective length of the intergluteal strip 8. Thus, this embodiment of the invention provides for adjustability of the intergluteal strip's effect length by placement of the attachment piece at a variable position along the intergluteal strip. This allows the user to shorten the effective length of the intergluteal strip to the desired amount.

In this embodiment the material used for cohesive adhesive is a latex-free synthetic rubber supplied by General Latex and coated by Bomarko. Use of these materials is well-known in the industry. A key parameter in application of these materials is dry coat weight, which affects the adhesive strength. The upper limit of the dry coat weight range is 3 lb/ream, at which point bleed-through occurs. At a dry coat weight of 1.78 lb/ream, an approximate bond strength results of 118.6 psi with a 5 lb roller bond. In the preferred embodiment, the dry coat weight is less than 1.78 lb/ream, so that the user can detach and reattach the attachment piece as many times as necessary to get the correct positioning.

Figure 19A:
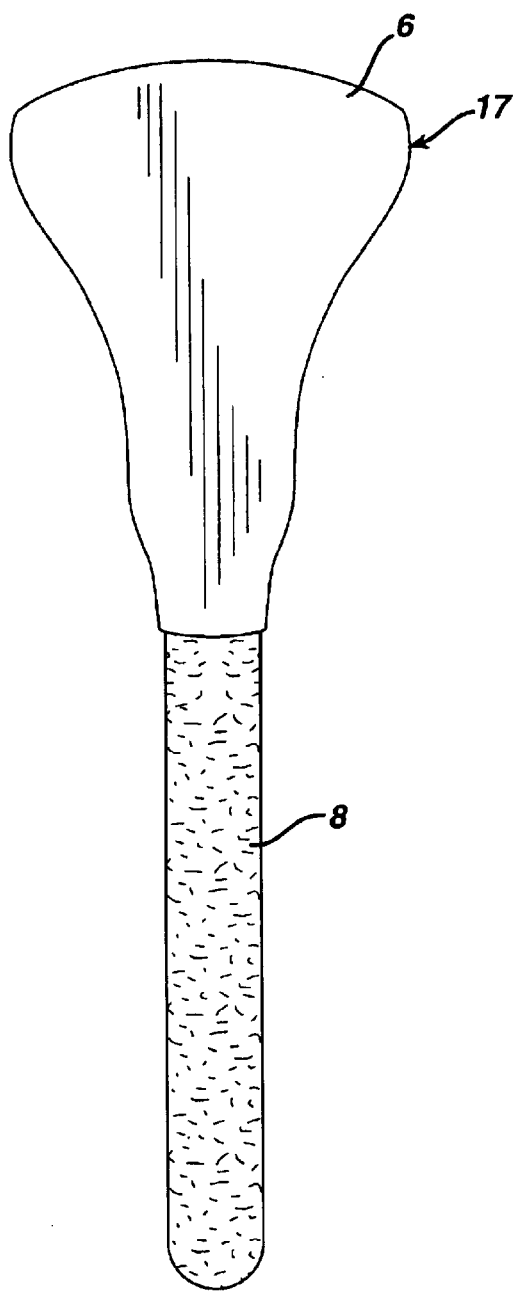
FIGS. 19A–19C depict a top view of an alternative embodiment in which an attachment piece is variably located along the length of the strip and secured by an adhesive area and slits located on the attachment piece.
Figure 19B:
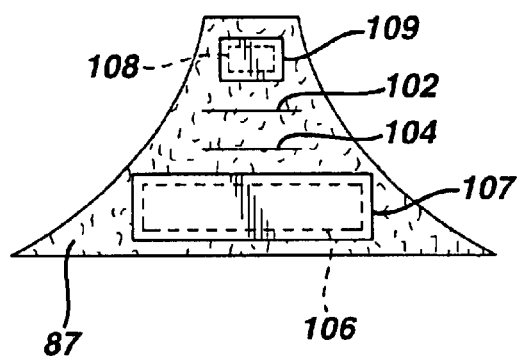

FIG. 19 shows the plan view of another alternative embodiment of the invention having adjustability of the intergluteal strip attained by using slots in the attachment piece 87. FIG. 19A shows the main pad body 17 and the intergluteal strip 8. FIG. 19B shows the plan view of the garment-facing side of the attachment piece 87. The attachment piece has two slots, slot A 102 and slot B 104. In use the intergluteal strip is looped through slot B 104 and then slot A 102. Once the desired amount is looped through, the user removes the release paper 109, revealing adhesive area 108 which serves to immobilize the intergluteal strip 8 to the attachment piece 87. The user would then remove the release paper 107 to expose an additional adhesive area which is used to secure the attachment piece to the user's undergarment.

Figure 19C:
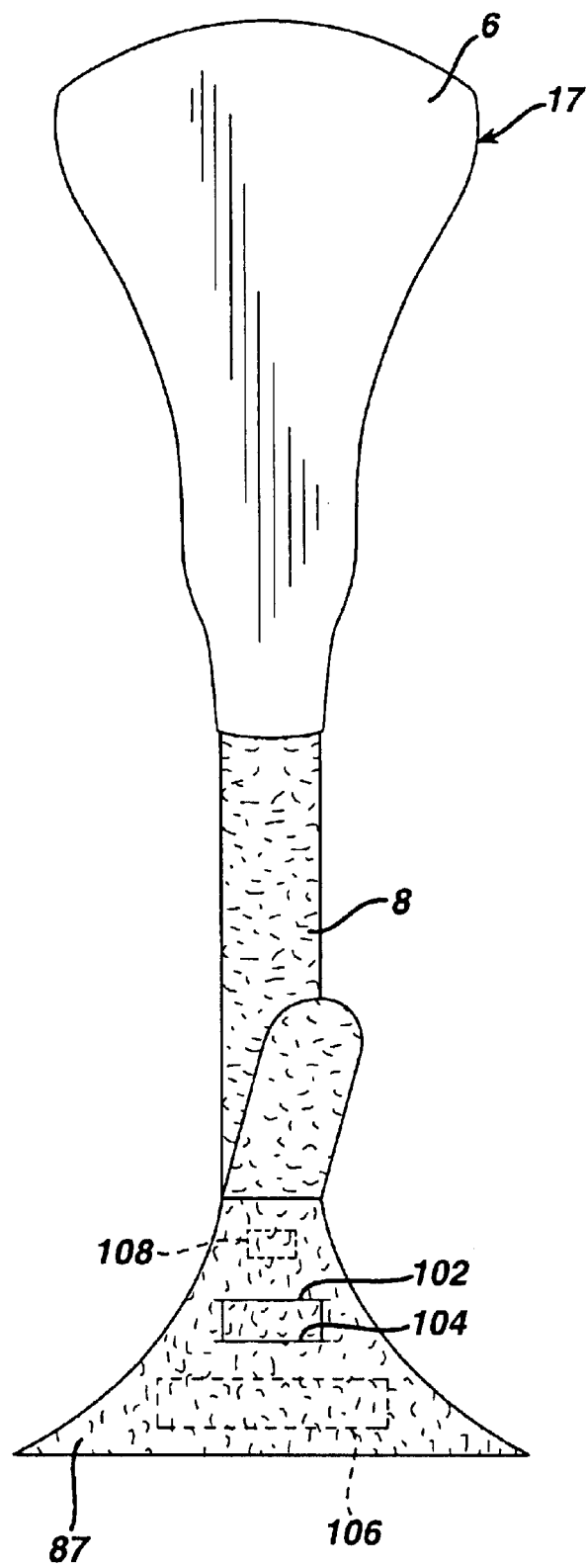

FIG. 19C shows the plan view of this embodiment of the invention with the intergluteal strip 8 looped through slots A and B, 102 and 104 respectively. The effective length of the intergluteal strip 8 is thereby shortened.

Slots A and B can vary in size and spacing. The width must be greater than the width of the intergluteal strip 8, which in the preferred embodiment is 20 mm. The width cannot be too great because it would then compromise the strength of the attachment piece adhesive area 108. Additionally, too wide a slot would not hold the intergluteal strip snugly enough. The maximum width is therefore about 5 mm on each end beyond the width of the intergluteal strip. The range of slot width, then, for an intergluteal strip width of 20 mm, is 22 to 30 mm. The slot height can vary between 0.5 and 5 mm. The minimum spacing of the slots is 1 cm. More closely spaced slots make it awkward for the user to loop the intergluteal strip through. Preferably, the spacing is 1.5 cm.

The size of the attachment piece adhesive area 108 used to immobilize the strip in this embodiment can vary in height and width. Preferably, its width is close to, but less than, the width of the intergluteal strip 8. In the preferred embodiment with an intergluteal strip width of 20 mm, the attachment piece adhesive area 108 has a width which can range from 12 to 19 mm. Preferably, the width is 18 mm. The height of the attachment piece adhesive area 108 depends on the height of the attachment piece 87 and how much room exists. With an attachment piece 5 cm high, the height of the attachment piece adhesive area 108 can vary from 8 to 15 mm. Preferably, the height is 10 mm. The shape of attachment piece adhesive area 108 as shown in FIGS. 19A–C is rectangular, but it could be any number of shapes, including square, circular, stripes or other.

In the above embodiments comprising an attachment piece 87 (depicted in FIGS. 17–19), the material used for the attachment piece 87 can be any nonwoven or woven fabric, film, or nonwoven/film laminate suitable for skin contact. Preferably, the material has stretch in the cross-direction (width-wise), so that in use, it can help stabilize the depth of the strip into the intergluteal crevice. Further, the shape of the attachment piece 87 can vary in length and width. In the preferred embodiment, it provides some stabilization for the depth of the strip by having a width or at least 9 cm, but the width could vary from 6 to 20 cm. The height of the attachment piece 87 is approximately 2.5 cm but can be as high as 8 cm. Preferably the height is approximately 5 cm. The top edge of the attachment piece need not be straight as indicated by the figures, but rather could be curved concavely or convexly to more closely approximate the triangular region of a thong undergarment. Further, the shape of the adhesive areas 91 and 106 need not be rectangular as shown in FIGS. 17–19, but can approximate the shape of the attachment piece as well. It could also be a rectangle with wider width so that the attachment piece 87 can provide the maximum amount of stabilization. Moreover, the invention is not limited to the presence of garment adhesive on the attachment piece. Alternative embodiments include the use of body adhesive as well as the absence of any adhesive on the attachment piece.

In addition with respect to the above embodiments, the shape of the VELCRO hook material 89 and cohesive adhesive 93 on the attachment piece 87 is depicted as square, but could be triangular, circular or other. The width must be less than that of the intergluteal strip 8. With a preferred intergluteal strip width of 2 cm, the width of the VELCRO hook material 89 and cohesive adhesive 93 can range from 0.5 cm to 2 cm. Preferably, the width is close to the maximum, 1.8 to 1.9 cm. The height of the VELCRO hook material 89 and cohesive adhesive 93 depends on the height of the attachment piece 87. In can vary between 25 and 95% of the height of the attachment piece. Preferably it is 60% of the height of the attachment piece.

Figure 20A:
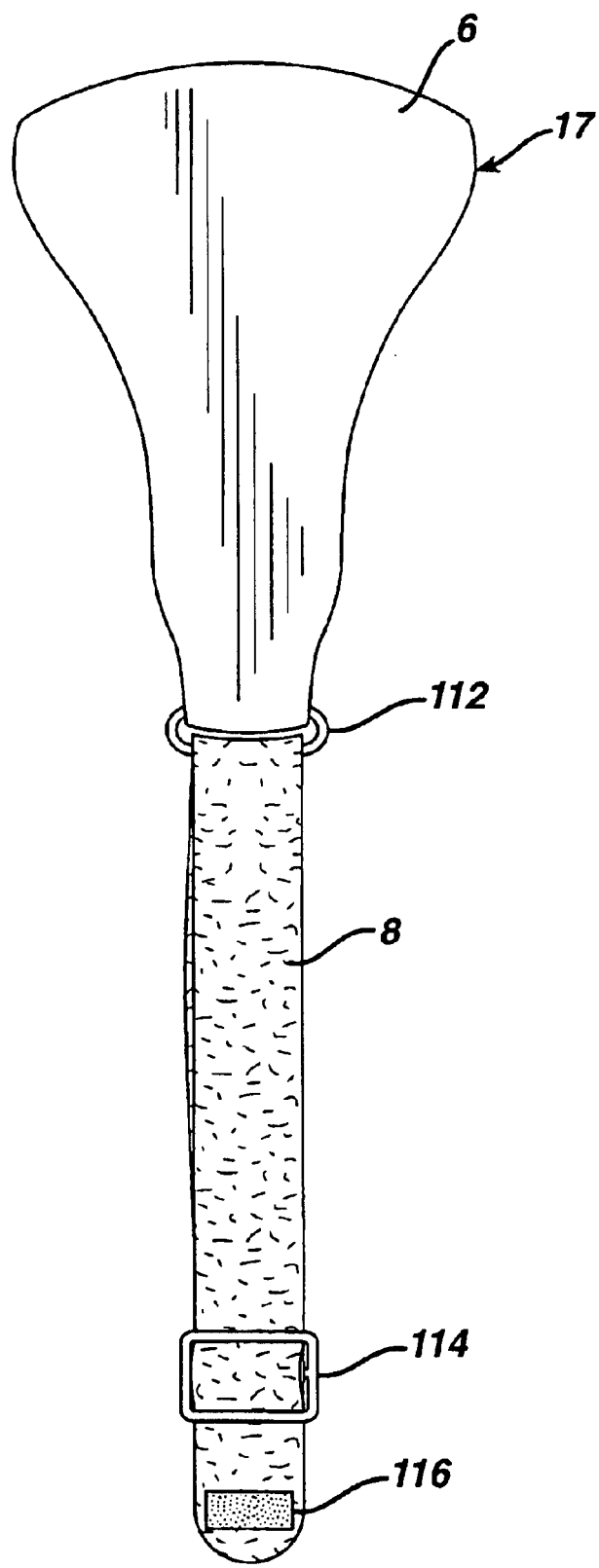
FIGS. 20A and 20B depict a top view of an alternative embodiment in which a ring and buckle arrangement is used to vary the length of the strip.

FIG. 20A shows the plan view of another alternative embodiment of the invention with adjustability of the intergluteal strip through means of a "bra strap" configuration having a ring 112 and buckle 114. The intergluteal strip 8 is looped through the ring 112 and buckle 114. FIG. 20A depicts the presence of an optional adhesive swatch 116 which prior to use is covered by a release paper and is used to attach the distal end of the intergluteal strip to the user's undergarment. The user can adjust the length of the intergluteal strip by grasping the distal end of the intergluteal strip and moving the buckle 114. Moving the buckle 114 closer to the main pad body 17 makes the intergluteal strip longer; moving the buckle 114 farther from the main pad body 17 makes the intergluteal strip shorter.

Figure 20B:
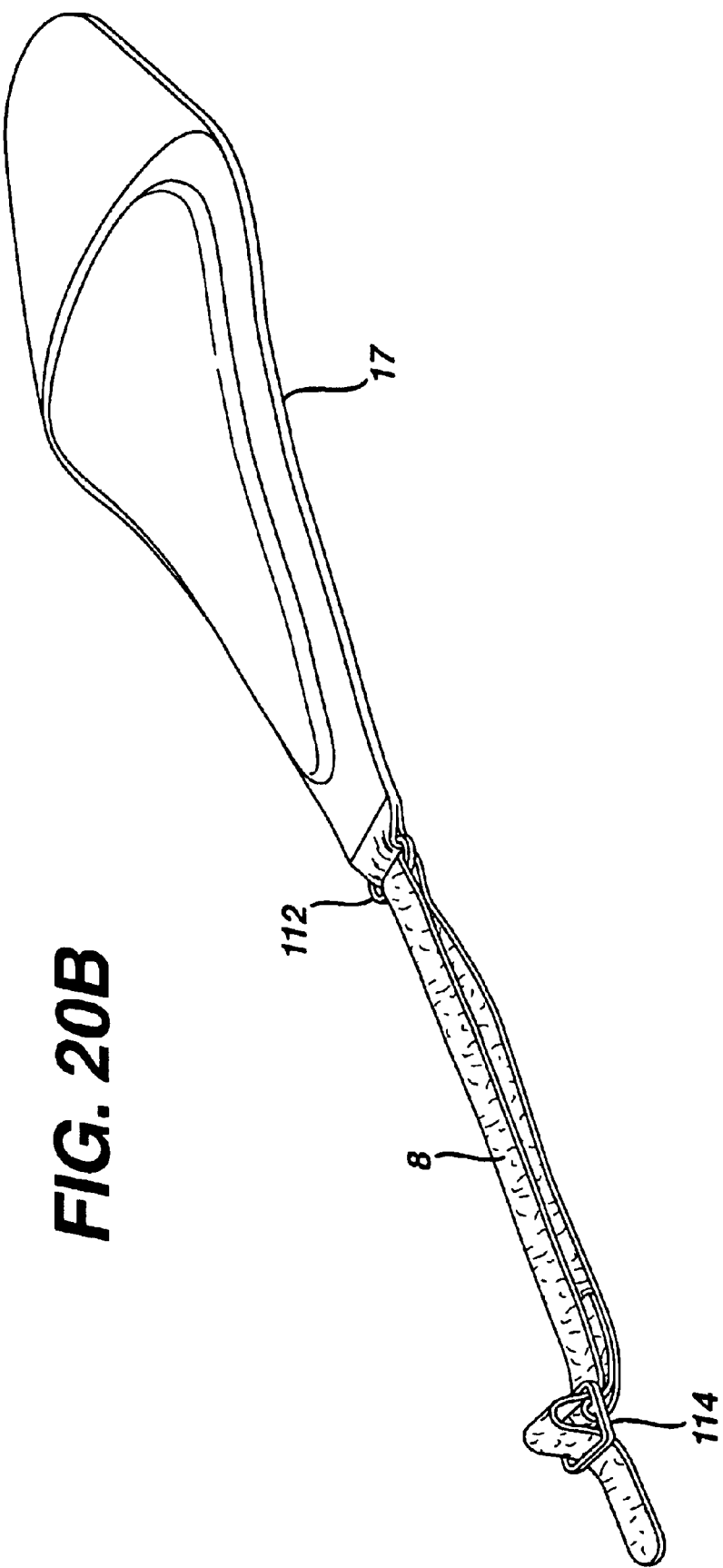
Figure 22A:
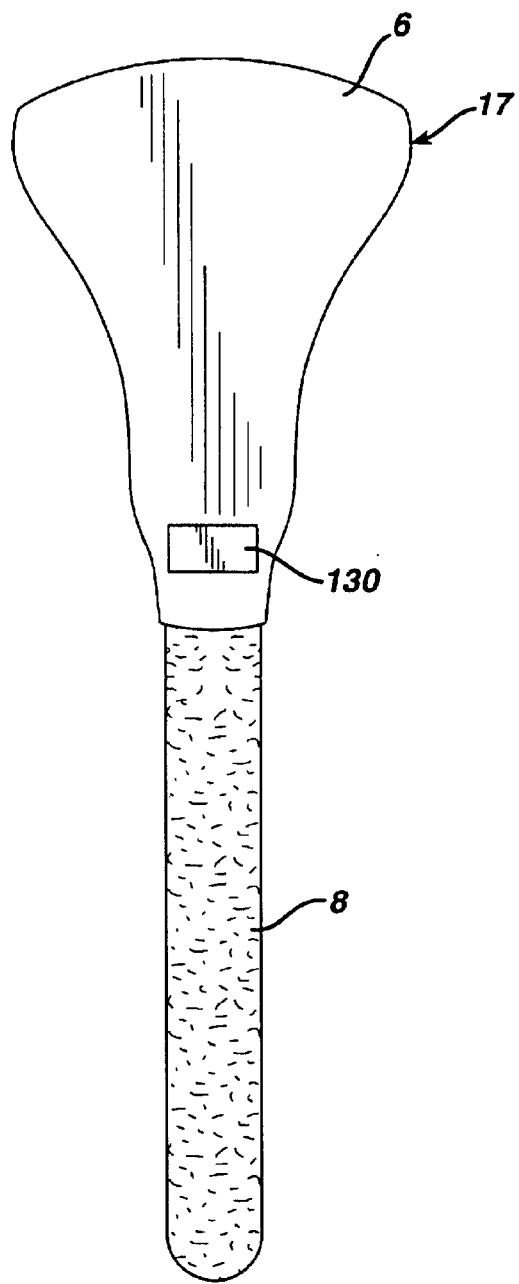
FIGS. 22A–22D depict a top view of an alternative embodiment wherein an adhesive swatch is used to retain a section of folded strip and thereby vary the length of the strip.
Figure 22B:
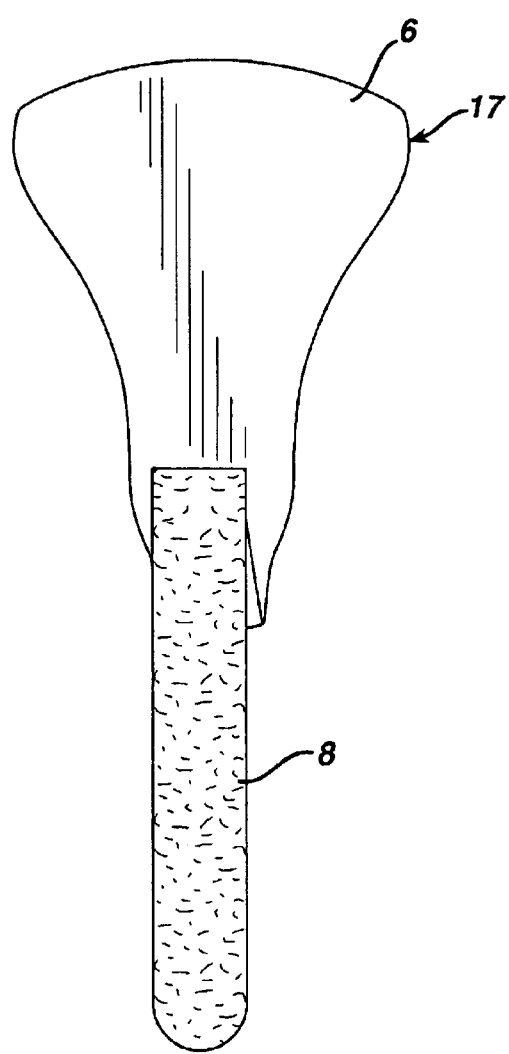
Figure 22C:
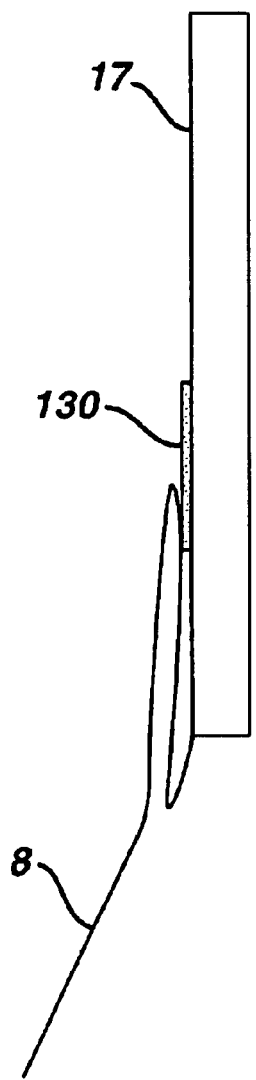
Figure 22D:
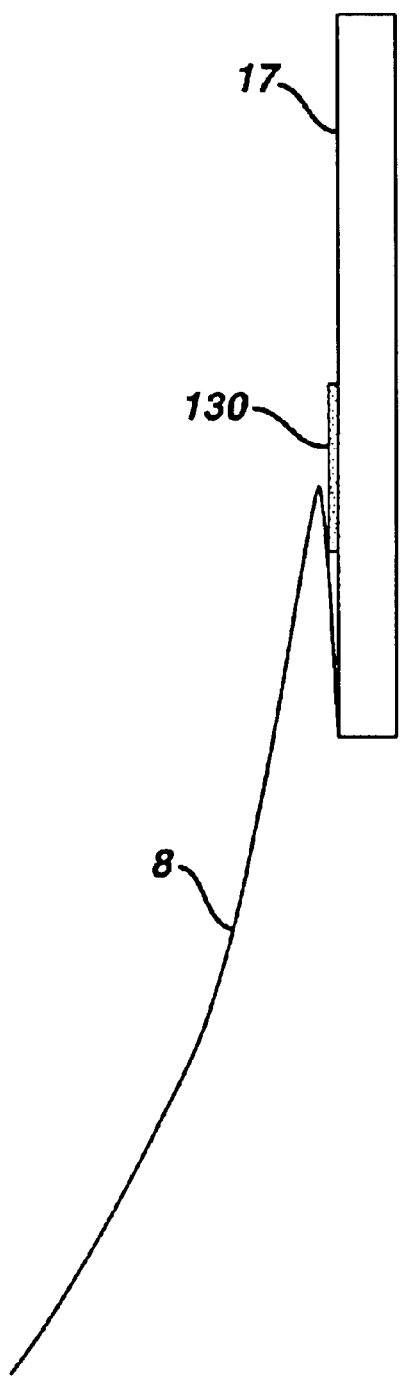

FIG. 20B illustrates the use of this embodiment of the invention. The size of the ring 112 and buckle 114 must be greater than the width of the intergluteal strip 8. In the preferred embodiment with an intergluteal strip width of 20 mm, this corresponds to an acceptable range of 22 to 30 mm for the inside diameter of both the ring 112 and buckle 114. The materials used for the ring and the buckle can be identical. In the preferred embodiment any rigid, medical-grade plastic would be a suitable material. It should be noted the invention is not so limited. As the invention includes the use of flexible, soft materials to perform the function of the buckle and the ring.

FIG. 21 shows a cross-sectional view of another alternative embodiment of the invention wherein the adjustability of the intergluteal strip 8 is attained through means of a sheath 120 which houses a pleated strip 8. That is, the pleated intergluteal strip 8 is housed between the barrier layer 6 and the sheath 120. In the preferred embodiment this sheath is made of the same material as the barrier layer and comprises an adhesive area 122 on the side that faces the strip 8. The user pulls out the strip to desired amount and presses down the sheath to secure the intergluteal strip with the adhesive. The adhesive used permits attachment and reattachment of the strip to permit securing of the pleated strip 8 prior to use and subsequent adjustment of the strip length by the user.

The size of the sheath 120 must be such that it extends longitudinally less than the end of the barrier layer 6. This is to ensure that the user easily differentiates the sheath film from the barrier film. The acceptable length and number of pleats can vary greatly. In general, if the pleats are more numerous and smaller, then precision in strip length is easier to achieve. For a strip length of 29.5 cm, 6 pleats of 3 cm length work well. Alternatively, 10 pleats of 2 cm length work as well. The length of the sheath must extend well beyond the length of the pleats, ensuring a secure housing area. For a 135 mm pad with 2 mm pleats, a 5 cm sheath length works well.

It is important for the width of the intergluteal strip to be less than the width of the main pad body 17 in the terminal region, since sufficient perimeter area is required to heat seal the sheath onto the film backing. At least 4 mm is required on each end. Therefore, for a main pad body width of 10 mm in its terminal region, the intergluteal strip width should be 2 mm. Conversely, for an intergluteal strip width of 20 mm, the main pad body should be 28 mm wide at its terminal region. In the preferred embodiment the adhesive is applied to the entire sheath area. If cost constraints are a concern, alternative embodiments are contemplated wherein a variety of patterns to minimize adhesive coverage could be employed.

FIG. 22 shows another alternative embodiment of the invention which contains an adhesive swatch and release paper (collectively 130) on the garment-facing side of the mouse pad body 17. The user can simply fold over the intergluteal strip 8 by the desired amount, remove the release paper, and affix the intergluteal strip to the adhesive swatch 130. This shortens the length of the intergluteal strip 8. FIG. 22A shows the intergluteal strip 8 at full length and FIG. 11B shows the intergluteal strip 8 shortened utilizing the adhesive swatch 130 of this invention. FIGS. 22C and 22D show a side view of this embodiment of the invention. In FIG. 22C, the intergluteal strip 8 is folded over and shortened by a greater amount than in FIG. 22D.

The size and shape of the adhesive swatch 130 can vary. Preferably, the width is close to, but less than, the width of the intergluteal strip 8. In the preferred embodiment with an intergluteal strip width of 20 mm, the adhesive swatch 130 has a width which can range from 12 to 19 mm. Most preferably, the width is 18 mm. The height of the adhesive swatch 130 can vary from 8 to 15 mm. Preferably, the height is 10 mm. The shapes of the adhesive swatch 130 as shown in FIG. 22 are rectangular, but could be any number of shapes, including square, circular, stripes, or other.

Figure 23A:
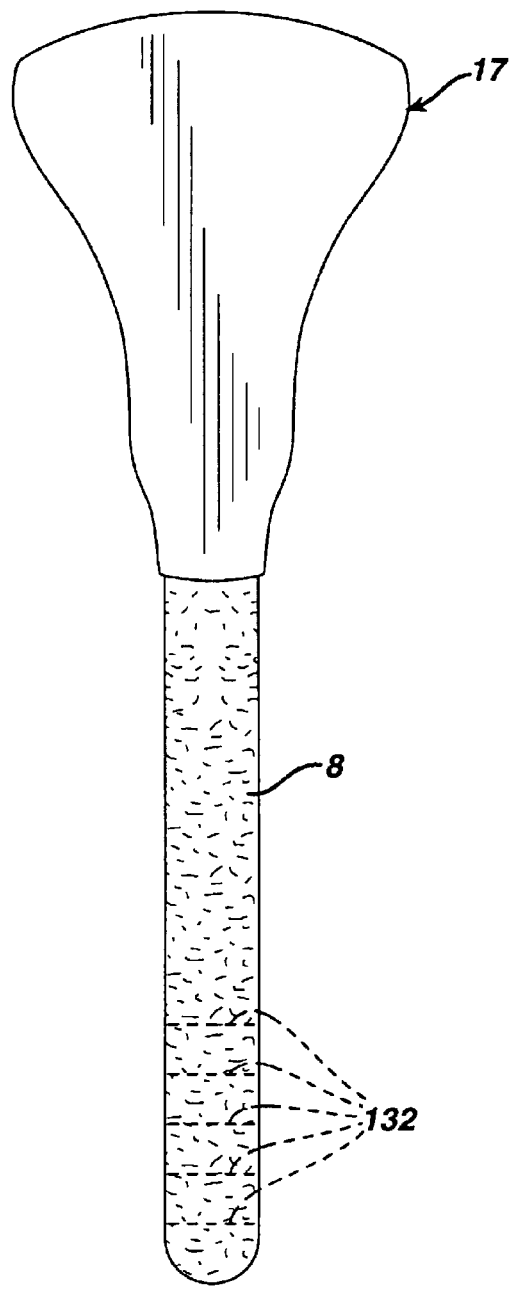
FIGS. 23A and 23B depict a top view of an alternative embodiment in which tear-off perforated sections of the strip are used to vary its length.
Figure 23B:
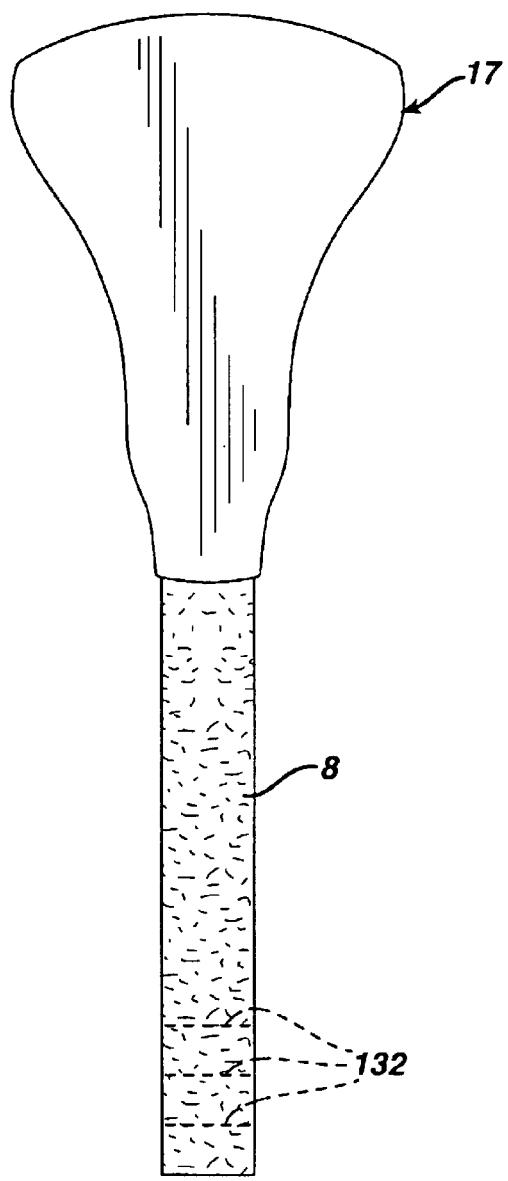

FIG. 23 depicts another alternative embodiment of the invention which consists of an intergluteal strip 8 which has a series of perforations 132 at the distal end. The user can then tear off the amount necessary at the appropriate perforation to thereby shorten the intergluteal strip to the desired length. FIG. 23A shows the intergluteal strip 8 at full length and FIG. 23B shows it shortened by tearing at the second perforation from the distal end.

The perforations 132 can vary in number and spacing. In the preferred embodiment the number of perforations can range from two to twenty. More preferably, the number of perforations ranges from three to eight. In the preferred embodiment the spacing between perforations can vary from 2 to 20 mm. More preferably the spacing is 10 mm. The preferable number and spacing of perforations are interrelated. If the spacing is greater, for example 20 mm, then the preferred number of perforations is smaller, for example 3. However, if the spacing is smaller, for example 10 mm, then the preferred number of perforations is greater, for example 6.

The slit width and number of the perforations 132 depend on the material properties of the intergluteal strip 8. In an embodiment having an elastic strip, the perforation slit width is large, since the remaining elastic strands are strong. For example, there may be 4 slits 3–5 mm wide, leaving 3 pieces of 1–2 mm wide fabric between the slits. For an intergluteal strip 8 material that is less elastic, the perforations could be composed of more uniform slits and fabric widths, for example 5 slits of 2 mm width and 5 pieces of 2 mm wide fabric.

Figure 24A:
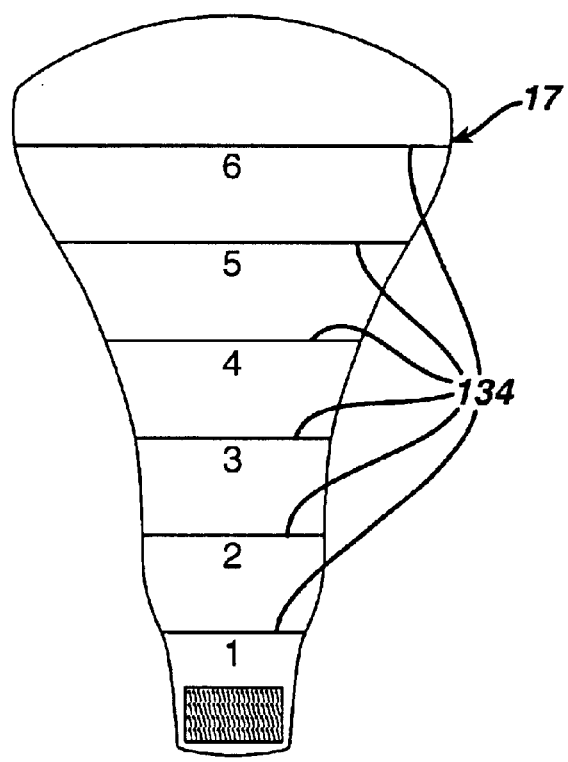
FIGS. 24A–24D depict a top view of an alternative embodiment wherein the strip is selectively attached at a position on the main pad body thereby adjusting the effective length of the strip.
Figure 24B:
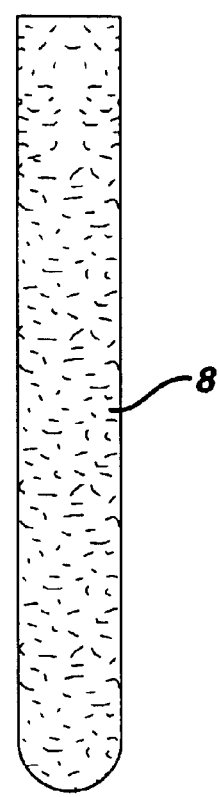
Figure 24C:
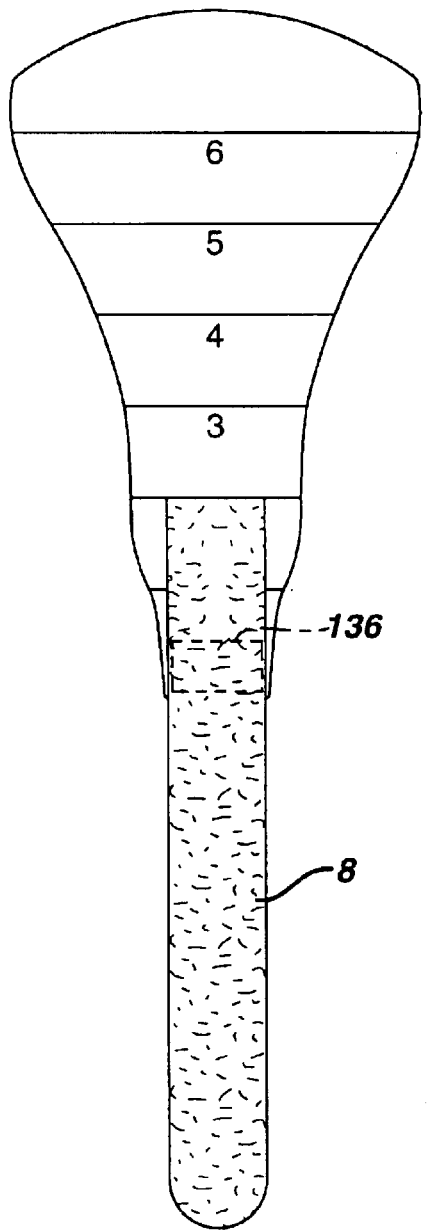
Figure 24D:
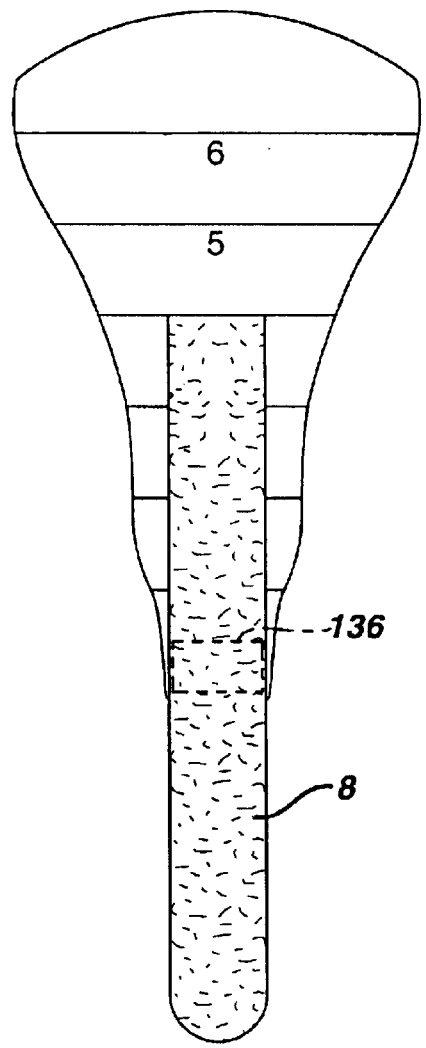

FIG. 24A shows another alternative embodiment of the invention which consists of a series of numbered gradations 134 and a hook swatch 136 on the garment-facing side of the main pad body 17. The intergluteal strip 8, shown in FIG. 24B, is not initially attached to the maid pad body 17. FIG. 24C and 24D both show how the user can attach the intergluteal strip 8 to the maid pad body 17 by positioning it at the appropriate numbered gradation 134 that shortens the intergluteal strip 8 to the desired length and then securing it at the hook and loop swatch 136. In FIG. 24D the intergluteal strip 8 is positioned at gradation #4, which shortens the effective length by an even greater amount than that indicated in FIG. 24C (where it is positioned at gradation #2).

The numbered gradations 134 can vary in quantity and spacing. In the preferred embodiment, the quantity of gradations can vary from two to ten, preferably six. In the preferred embodiment, the spacing between gradations can vary from 10 to 25 mm, preferably 18–20 mm.

In the preferred embodiment, the material for the hook swatch 136 must be suitable for the intergluteal strip 8 material to attach to by itself, without need for an extra loop swatch. Many hook-type materials work, including the traditional VELCRO, but a most preferred material, because of softness and bulk, is a material supplied by the 3M Corporation under the designation CS-600 Hook Material. This hook swatch 136 could also be replaced by an adhesive swatch.

The size and shape of the hook (or adhesive) swatch 136 can vary. Preferably, the width is close to, but less than, the width of the intergluteal strip 8. In the preferred embodiment with an intergluteal strip width of 20 mm, the hook swatch 136 has a width which can range from 12 to 19 mm. Most preferably, the width is 18 mm. The height of the hook swatch 136 can vary from 8 to 15 mm. Preferably, the height is 10 mm. The shape of the hook swatch 136 as shown in FIG. 24 are rectangular, but could be any number of shapes, including square, circular, stripes, or other.

Figure 25A:
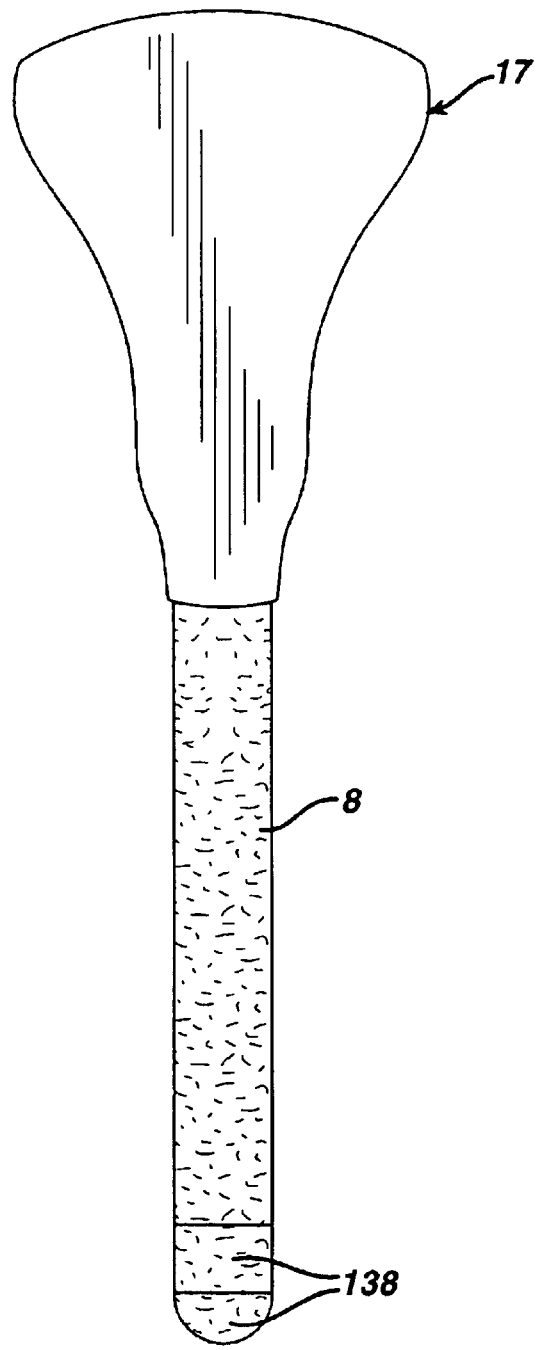
FIGS. 25A–25B and 26A–26C depict views of an alternative embodiment in which tear-off shingle sections of the strip are used to vary its length.
Figure 25B:
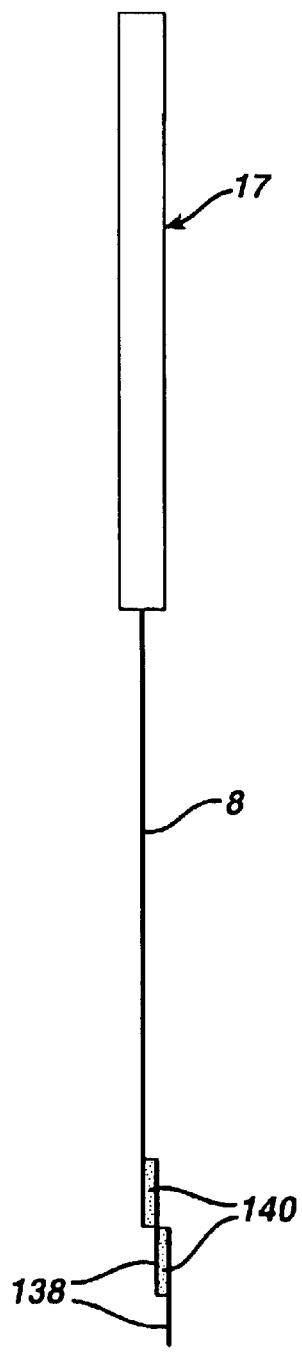
Figure 26C:
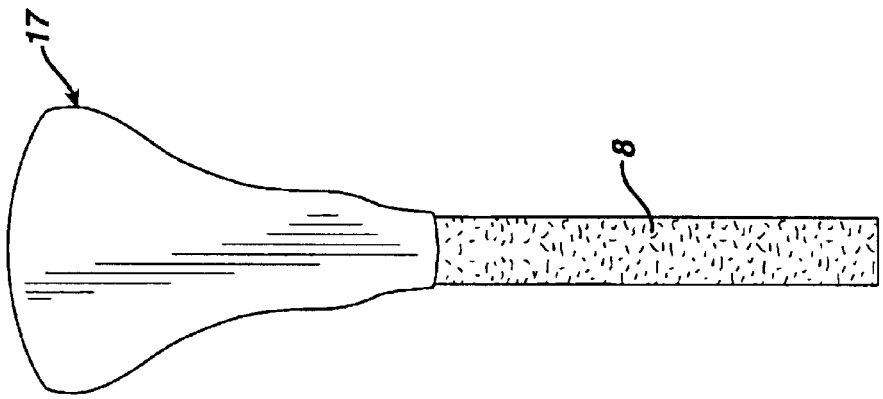
Figure 26B:
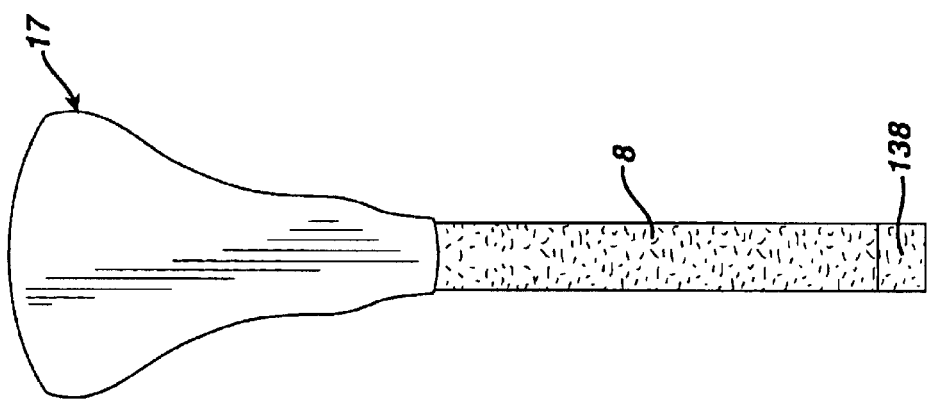
Figure 26A:
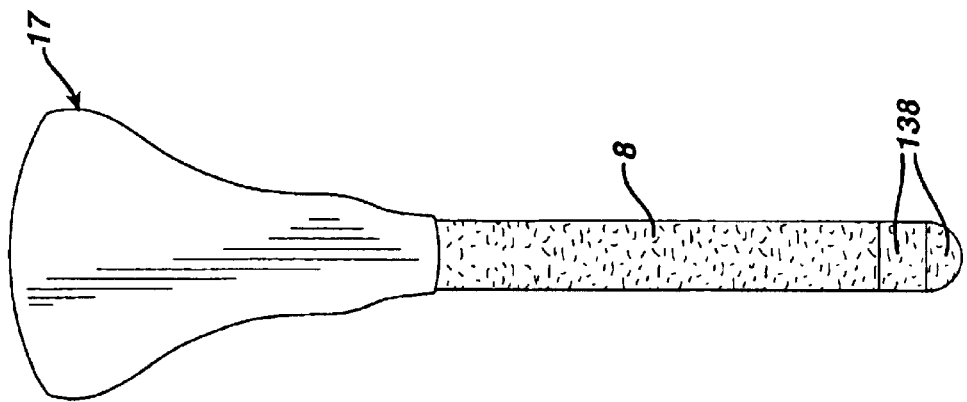

FIGS. 25A and 25B show another embodiment of the invention which consists of an intergluteal strip 8 having at its distal end a series of overlapping pieces or shingles 138. There is adhesive 140 between the shingles. The user can shorten the length of the intergluteal strip 8 by removing the requisite number of shingles 138 to achieve the desired length. FIGS. 26A–C show plan views of this embodiment. In FIG. 26A no shingles have been removed while one shingle has been removed in FIG. 26B, and two shingles have been removed in FIG. 26C. Accordingly, the length of the intergluteal strip 8 is shorter in FIG. 26B than in FIG. 26A and even shorter in FIG. 26C than in FIG. 26B.

The shingles 138 can vary in size and number. The number of shingles can range from two to twenty. Preferably, the number of shingles ranges from three to eight. The length of the shingles can vary from 5 to 20 mm. Preferably the length is 10 mm. The preferable number and length of perforations are interrelated. If the length is greater, for example than 20 mm, then the preferred number of shingles is smaller, for example 3. However, if the length is smaller, for example 10 mm, then the preferred number of perforations is greater, for example 6.

FIG. 27 illustrates a further embodiment of the invention wherein positioning adhesive 144 and release paper 142 are present on an intergluteal strip 8, and wherein one or more distal sections of which strip are configured to be removed in the adjustment process. Examples of these appear above wherein the strip 8 comprises shingles (reference FIG. 25) and wherein the strip 8 has perforations (reference FIG. 23).

In this embodiment, the release paper 142 is perforated. In FIG. 27A the user has not selected a length yet, so the release paper 142 is intact and the whole length of position adhesive is unexposed 144. In FIG. 27B the user has chosen to keep the intergluteal strip 8 at is full length and has removed the bottom third of the release paper only, exposing the positioning adhesive 146 at the distal end of the intergluteal strip 8. In FIG. 27C the user has chosen to shorten the strip be either tearing at the first perforation (reference FIG. 23) or removing the farthest shingle (reference FIG. 25). In either event, the bottom third of the release paper is torn off at the same time. The user then removes what was originally the middle third of the release paper, exposing the position adhesive 146 at the new distal end of the shortened intergluteal strip 8. If FIG. 27D, the user has chosen to further shorten the strip. The bottom ⅔ of the release paper is torn off at the same time. The user then removes the remaining third of the release paper, exposing the positioning adhesive 146 at the new distal end of the shortened intergluteal strip 8.

With respect to this embodiment, the size of the adhesive area 144 can vary. Preferably, the adhesive is slot coated as a strip, with a width more narrow than the width of the intergluteal strip 8. In the preferred embodiment with an intergluteal strip width of 20 mm, the adhesive 144 has a width which can range from 12 to 19 mm. Preferably, the width is 18 mm. The shape of the adhesive 144 can vary from a rectangular strip, and could be square, circular, stripes, or other.

In addition, the release paper 142 is preferably a siliconized polymer film, such as polyethylene. This gives the user a comfort advantage over paper when the unremoved portion, still affixed to the intergluteal strip, resides in the intergluteal crevice. The perforation slit width of the release paper 142 can vary, depending on the tensile properties of the material. The perforations should be of sufficient quantity to tear easily when needed, yet not tear accidentally when in use, which would expose the adhesive.

As to all of the above embodiments in which an adhesive swatch was present at the distal end of the intergluteal strip 8, this adhesive could alternatively be used for securing the intergluteal strip to the panty and for securing it to the user's body. In the latter case, a suitable bio-adhesive would be placed on the body facing side of the intergluteal strip. A further alternative would be the absence of any adhesive on the distal end of the intergluteal strip in which case the intergluteal strip would stay in place through frictional contact with the intergluteal crevice.

While the invention has been described with reference to the above alternative embodiments thereof, it will be appreciated by those of ordinary skill in the art that various modifications can be made to the structure and function of the individual parts of the system without departing from the spirit and scope of the invention as a whole.

We claim:

1. A feminine hygiene pad comprising:

a main pad body having an absorbent core positioned between a cover material and a barrier layer, a rear end which in use is located in proximity to a wearer's buttocks and an opposed front end, a first face adapted to contact with the wearer's body and ax opposing second face adapted to face toward an undergarment of the wearer, a main pad body thickness being defined as the dimension of the main pad body from the first face to the opposing second face, said main pad body adapted to be worn in close proximity to the vagina of the wearer;

said absorbent core being adapted to not significantly extend beyond the anterior portion of the perineum of the wearer in use;

said feminine hygiene pad further comprising a strip, said strip being substantially planar and relatively small in thickness compared to the main pad body thickness, and said strip extending rearwardly from said rear end of the main pad body, terminating at a distal end and having a length as measured from said rear end of the main pad body to the distal end;

wherein the strip has a width substantially along its entire length that is less than a width of the rear end of the main pad body, and wherein said feminine hygiene pad being configured such that said strip is adapted to be received between the buttocks of the wearer to thereby facilitate retaining said main pad body adjacent to the wearer's vagina; and said feminine hygiene pad further comprising an adjustment means whereby the length of said strip is adjustable by the wearer.

2. A feminine hygiene pad as recited in claim 1, wherein said main pad body is between 8 and 13.1 cm in length.

3. A feminine hygiene pad as recited in claim 1, wherein said strip is less than 1 cm in thickness.

4. A feminine hygiene pad as recited in claim 1, wherein said strip is between 0.5 cm and 2.5 cm in width.

5. A feminine hygiene pad as recited in claim 1, wherein said opposing second face comprises an area of adhesive to aid in retaining said main pad body adjacent to the wearer's vagina.

6. A feminine hygiene pad as recited in claim 1, wherein said feminine hygiene pad further comprises a front flap, extending forwardly from the front end of the main pad body and terminating at a distal end, said flap adapted to aid in retaining said main pad body adjacent to the wearer's vagina.

7. A feminine hygiene pad as recited in claim 6, wherein said front flap is stretchable.

8. A feminine hygiene pad as recited in claim 6, wherein said distal end of said front flap contains an area of adhesive adapted for attaching said distal end to said undergarment of the wearer.

9. A feminine hygiene pad as recited in claim 6, wherein said front flap contains an area of body adhesive adapted for attaching said distal end to the wearer's body.

10. A feminine hygiene pad as recited in claim 1, wherein said strip is flexible.

11. A feminine hygiene pad as recited in claim 1, wherein said adjustment means is non elastic.

12. A feminine hygiene pad as recited in claim 1, wherein said adjustment means comprises one or more loops positioned on said opposing second face whereby in use the length of the strip is capable of being reduced by looping the distal end of the strip through one or more of said loops.

13. A feminine hygiene pad as recited in claim 1, wherein said adjustment means comprises a ring and buckle arrangement.

14. A feminine hygiene pad as recited in claim 1, wherein said adjustment means comprises a section of the strip, located adjacent to the main pad body, said section being folded into one or more pleats, said one or more pleats being held in position by means of an adhesive releaseably securing said section of the strip to a sheath; whereby in use the length of the strip is capable of being adjusted by releasing said adhesive, unfolding the one or more of said pleats and reattaching said adhesive.

15. A feminine hygiene pad as recited in claim 1, wherein said adjustment means comprises an adhesive swatch positioned on the opposing second face whereby in use the length of the strip is capable of being reduced by making a fold in the strip and securing said fold to the adhesive swatch.

16. A feminine hygiene pad as recited in claim 1, wherein said adjustment means comprises said strip containing one or more perforated lines, said one or more perforated lines extending across the width of said strip and thereby creating one or more preferential tearing lines, whereby in use the length of the strip is capable of being reduced by removing one or more sections of the distal end of said strip by tearing along said one or more preferential tearing lines.

17. A feminine hygiene pad as recited in claim 16, wherein the distal end of said strip contains an area of positioning adhesive which, prior to use is covered by an area of release paper; and wherein each of said one or more perforated lines creates a corresponding tearing line in the release paper.

18. A feminine hygiene pad as recited in claim 1, wherein said adjustment means comprises said strip containing one or more overlapping shingles at its distal end whereby in use the length of the strip is capable of being reduced by removing said one or more shingles.

19. A feminine hygiene pad comprising:

a main pad body having an absorbent core positioned between a cover material and a barrier layer, a rear end which in use is located in proximity to a wearer's buttocks and an opposed front end, a first face adapted to contact with the wearer's body and an opposing second face adapted to face toward an undergarment of the wearer, a main pad body thickness being defined as the dimension of the main pad body from the first face to the opposing second face, said main pad body adapted to be worn in close proximity to the vagina of the wearer;

said absorbent core being adapted to not significantly extend beyond the anterior portion of the perineum of the wearer in use;

said opposing second face comprising a strip attachment means;

a strip having a proximal end and a distal end, said strip releaseably attachable by said strip attachment means to the main pad body, said strip being substantially planar and relatively small in thickness compared to the thickness of the main pad body, and said strip once attached to said main pad body extending rearwardly from said rear end of the main pad body, terminating at the distal end and having an effective length as measured from said rear end of the main pad body to the distal end; wherein the strip has a width substantially along its entire length that is less than a width of the rear end of the main pad body; and wherein said feminine hygiene pad being configured such that said strip is adapted to be received between the buttocks of the wearer to thereby facilitate retaining said main pad body adjacent to the wearer's vagina: and whereby the effective length of the strip is adjustable by the wearer by attaching the strip by said strip attachment means at a point on the strip in between the proximal and distal ends of the strip.

20. A feminine hygiene pad as recited in claim 19, wherein the opposing second face comprises a series of numbered gradations as an aide to the wearer in adjusting the length of the strip.

21. A feminine hygiene pad as recited in claim 19, wherein the strip attachment means comprises an adhesive swatch.

22. A feminine hygiene pad as recited in claim 19, wherein the strip attachment means comprises a hook and loop fastening material.

23. A feminine hygiene pad comprising:

a main pad body having an absorbent core positioned between a cover material and a barrier layer, a rear end which in use is located in proximity to a wearer's buttocks and an opposed front end, a first face adapted to contact with the wearer's body and an opposing second face adapted to face toward an undergarment of the wearer, a main pad body thickness being defined as the dimension of the main pad body from the first face to the second face, said main pad body adapted to be worn in close proximity to the vagina of the wearer;

said absorbent core being adapted to not significantly extend beyond the anterior portion of the perineum of the wearer in use;

said feminine hygiene pad further comprising a strip, said strip being substantially planar and relatively small in thickness compared to the main pad body thickness, and said strip extending rearwardly from said rear end of the main pad body, terminating at a distal end and having a length from said rear end of the main pad body to the distal end; an attachment piece releaseably affixed by a positioning means to said strip at a distance from the distal end selectable by the wearer, thereby establishing an effective length of the strip as measured from said rear end of the main pad body to the attachment piece; and wherein said feminine hygiene pad being configured such that said strip is adapted to be received between the buttocks of the wearer to thereby facilitate retaining said main pad body adjacent to the wearer's vagina.

24. A feminine hygiene pad as recited in claim 23, wherein said attachment piece comprises an area of garment adhesive.

25. A feminine hygiene pad as recited in claim 23, wherein said attachment piece comprises an area of body adhesive.

26. A feminine hygiene pad as recited in claim 23, wherein said positioning means comprises a hook and loop fastening material.

27. A feminine hygiene pad as recited in claim 23, wherein said positioning means comprises a cohesive adhesive zone.

28. A feminine hygiene pad as recited in claim 23, wherein said positioning means comprises two or more slits in the attachment piece, whereby in use the strip is looped through said two or more slits and secured by means of an adhesive area on the attachment piece.

* * * * *